US011224761B1

(12) United States Patent
Wazer et al.

(10) Patent No.: US 11,224,761 B1
(45) Date of Patent: Jan. 18, 2022

(54) RADIOACTIVE THERAPEUTIC DEVICE

(71) Applicants: David E. Wazer, Westwood, MA (US); Thomas A. DiPetrillo, Dover, MA (US); John J. Munro, III, North Andover, MA (US)

(72) Inventors: David E. Wazer, Westwood, MA (US); Thomas A. DiPetrillo, Dover, MA (US); John J. Munro, III, North Andover, MA (US)

(73) Assignee: PointSource Technologies, LLC, Boston, MA (US)

( * ) Notice: Subject to any disclaimer, the term of this patent is extended or adjusted under 35 U.S.C. 154(b) by 111 days.

(21) Appl. No.: 16/688,392

(22) Filed: Nov. 19, 2019

(51) Int. Cl.
*A61N 5/10* (2006.01)
*G21G 4/08* (2006.01)

(52) U.S. Cl.
CPC ............ *A61N 5/1007* (2013.01); *G21G 4/08* (2013.01)

(58) Field of Classification Search
CPC .. A61N 5/1001; A61N 5/1007; A61N 5/1027; A61N 5/1028; A61N 5/1029; A61N 2005/1024; A61N 2005/1025; A61B 17/0644
See application file for complete search history.

(56) References Cited

U.S. PATENT DOCUMENTS

| 4,754,745 | A | 7/1988 | Horowitz |
| 4,815,449 | A | 3/1989 | Horowitz |
| 4,936,823 | A | 6/1990 | Colvin et al. |
| 5,030,195 | A | 7/1991 | Nardi |
| 5,460,592 | A | 10/1995 | Langton et al. |
| 5,626,592 | A | 5/1997 | Phillips et al. |
| 5,713,911 | A | 2/1998 | Racenet et al. |
| 5,830,221 | A | 11/1998 | Stein et al. |
| 5,906,573 | A | 5/1999 | Aretz |
| 6,010,446 | A | 1/2000 | Grimm |
| 6,030,333 | A | 2/2000 | Sioshansi et al. |
| 6,146,322 | A | 11/2000 | Papirov et al. |
| 6,264,596 | B1 | 7/2001 | Weadock |
| 6,264,599 | B1 | 7/2001 | Slater et al. |
| 6,293,899 | B1 | 9/2001 | Sioshansi et al. |
| 6,419,621 | B1 | 7/2002 | Sioshansi et al. |
| 6,436,026 | B1 | 8/2002 | Sioshansi et al. |

(Continued)

FOREIGN PATENT DOCUMENTS

EP    1 126 900    8/2001

*Primary Examiner* — Carrie R Dorna
(74) *Attorney, Agent, or Firm* — David M. Driscoll, Esq.

(57) ABSTRACT

A brachytherapy source delivery device includes a first tissue-piercing leg having proximal and distal ends, a second tissue-piercing leg having proximal and distal ends, wherein the proximal ends of the first and second tissue-piercing legs are joined at a span section in a first angular orientation with respect to each other, and a carrier element formed at, or attached to, the span section, the carrier element configured to support a radioactive brachytherapy source. The distal ends of the first and second legs can be curved inward toward each other to pierce a tissue when engaged toward each other into a closed position. The first and second tissue-piercing legs can be formed of a wire having a circular cross-sectional or non-circular cross-sectional shape. The carrier element can be tangentially attached to the span section. Each of the legs have a length that is greater than the length of the span section.

21 Claims, 32 Drawing Sheets

(56) References Cited

U.S. PATENT DOCUMENTS

| | | |
|---|---|---|
| 6,471,630 B1 | 10/2002 | Sioshansi et al. |
| 6,527,693 B2 | 3/2003 | Munro, III et al. |
| 6,547,812 B1 | 4/2003 | Hu |
| 6,575,887 B1 | 6/2003 | Schrayer |
| 6,575,888 B2 | 6/2003 | Zamora et al. |
| 6,589,502 B1 | 7/2003 | Coniglione et al. |
| 6,599,230 B2 | 7/2003 | Hastings et al. |
| 6,616,592 B1 | 9/2003 | Rosenthal et al. |
| 6,629,988 B2 | 10/2003 | Weadock |
| 6,659,933 B2 | 12/2003 | Asano |
| 6,709,381 B2 | 3/2004 | Munro, III |
| 6,749,553 B2 | 6/2004 | Brauckman et al. |
| 6,761,680 B2 | 7/2004 | Terwilliger et al. |
| 6,773,390 B2 | 8/2004 | McDaniel |
| 6,786,858 B2 | 9/2004 | Terwilliger et al. |
| 6,820,318 B2 | 11/2004 | Terwilliger et al. |
| 6,926,733 B2 | 8/2005 | Stinson |
| 6,969,344 B2 | 11/2005 | Drobnik et al. |
| 6,997,862 B2 | 2/2006 | Terwilliger et al. |
| 7,008,368 B2 | 3/2006 | Terwilliger et al. |
| 7,060,020 B2 | 6/2006 | Terwilliger et al. |
| 7,070,554 B2 | 7/2006 | White et al. |
| 7,105,018 B1 | 9/2006 | Yip et al. |
| 7,604,586 B2 | 10/2009 | Wazer et al. |
| 7,942,931 B2 | 5/2011 | Gonzalez et al. |
| 7,972,260 B2 | 7/2011 | Wazer et al. |
| 8,061,520 B2 | 11/2011 | Stopek |
| 8,069,980 B2 | 12/2011 | Stopek et al. |
| 8,114,007 B2 | 2/2012 | Lamoureux et al. |
| 8,267,849 B2 | 9/2012 | Wazer et al. |
| 8,292,068 B2 | 10/2012 | Stopek et al. |
| 8,342,376 B2 | 1/2013 | Surti |
| 8,366,598 B2 | 2/2013 | Lamoureux et al. |
| 8,403,946 B2 | 3/2013 | Whitfield et al. |
| 8,454,489 B2 | 6/2013 | Drobnik et al. |
| 8,486,047 B2 | 7/2013 | Stopek |
| 8,529,819 B2 | 9/2013 | Ostapoff et al. |
| 8,551,132 B2 | 10/2013 | Eskridge et al. |
| 8,579,785 B2 | 11/2013 | Shariati |
| 8,678,990 B2 | 3/2014 | Wazer et al. |
| 8,939,153 B1 | 1/2015 | Reicher et al. |
| 9,198,654 B1 | 12/2015 | Reicher et al. |
| 9,763,660 B2 | 9/2017 | Wazer et al. |
| 10,159,850 B2 | 12/2018 | Racenet et al. |
| 10,286,227 B2 | 5/2019 | Munro, III et al. |
| 10,293,553 B2 | 5/2019 | Racenet et al. |
| 2002/0010480 A1 | 1/2002 | Sancoff et al. |
| 2004/0192998 A1 | 9/2004 | Brauckman et al. |
| 2006/0278679 A1* | 12/2006 | Viola .................. A61B 17/0644 227/155 |
| 2006/0282118 A1* | 12/2006 | Surti .................. A61B 17/0682 606/219 |
| 2007/0021642 A1* | 1/2007 | Lamoureux .......... A61N 5/1027 600/4 |
| 2009/0012347 A1 | 1/2009 | Helle et al. |
| 2009/0018535 A1 | 1/2009 | Schechter et al. |
| 2011/0245578 A1 | 10/2011 | Wazer et al. |
| 2012/0125792 A1 | 5/2012 | Cassivi |
| 2014/0066688 A1 | 3/2014 | Cassivi |
| 2018/0185670 A1* | 7/2018 | Kostrzewski ...... A61B 17/0644 |
| 2019/0126066 A1 | 5/2019 | Racenet et al. |

* cited by examiner

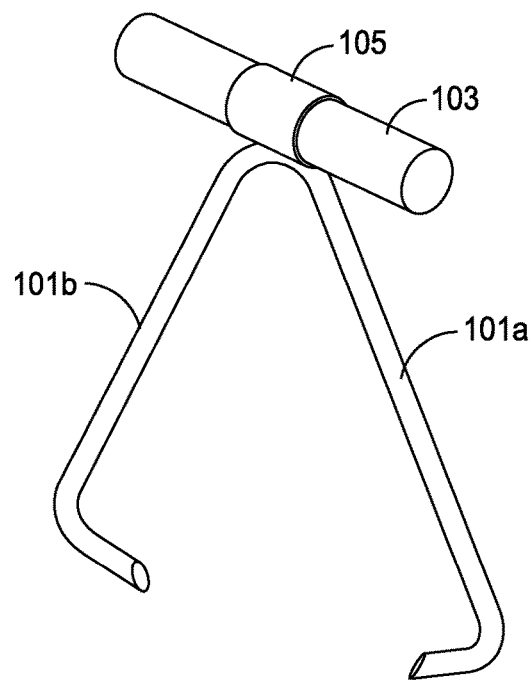
FIG. 9A
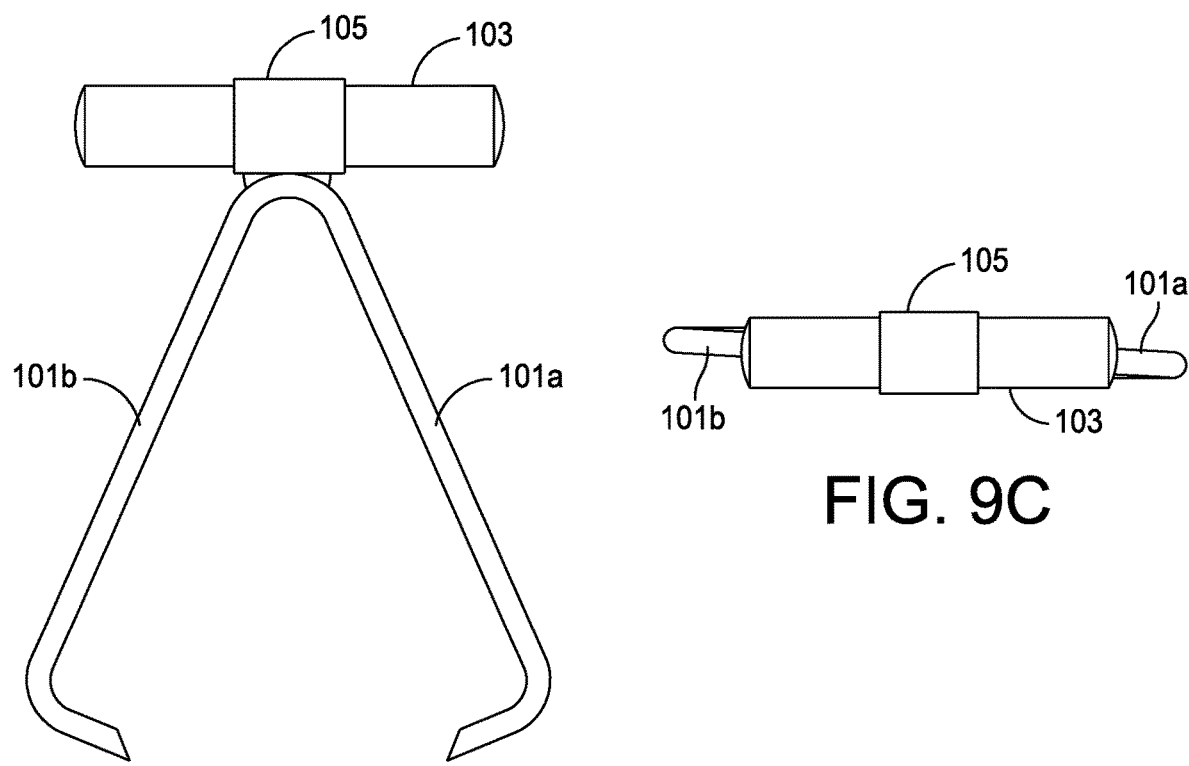
FIG. 9C
FIG. 9B

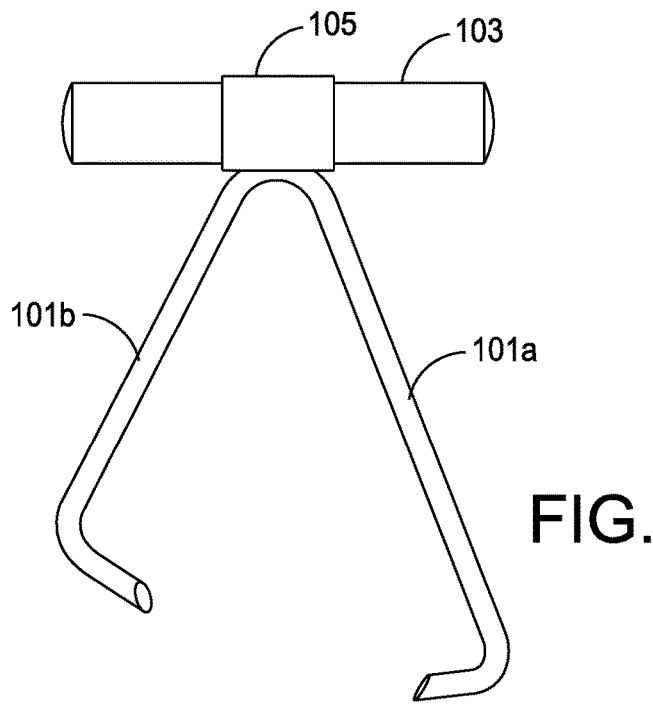
FIG. 10A
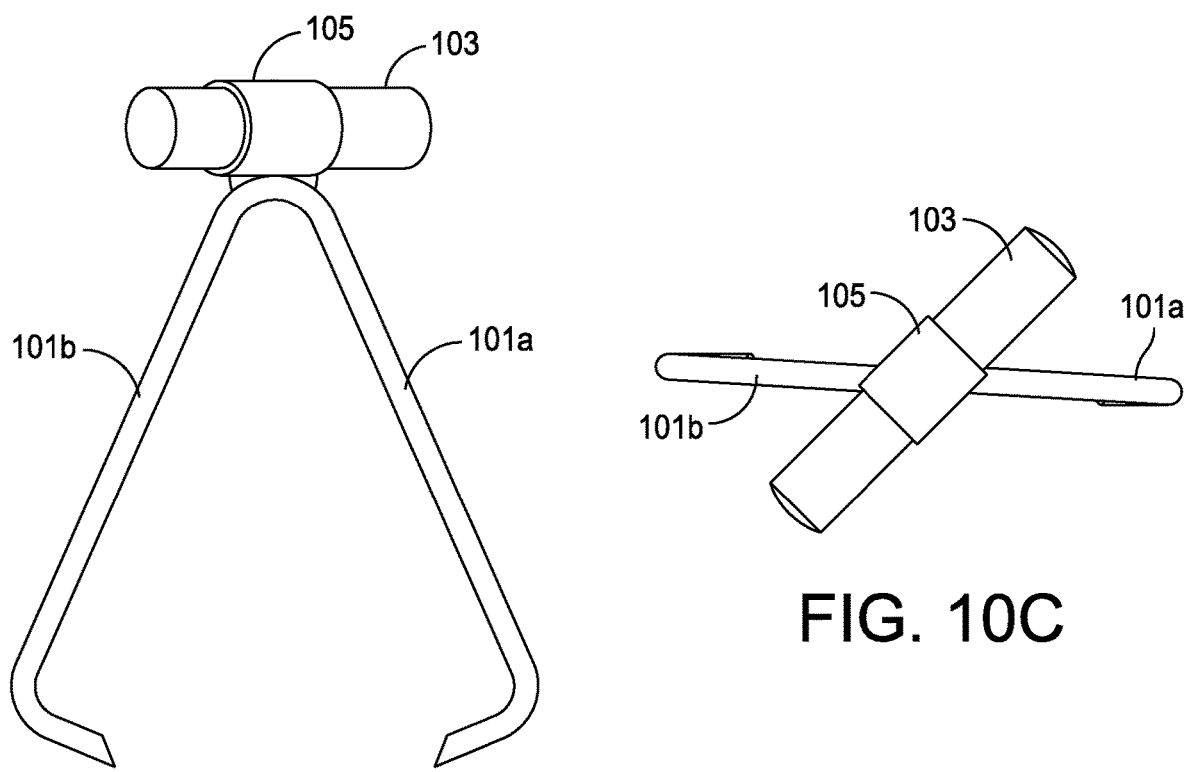
FIG. 10B
FIG. 10C

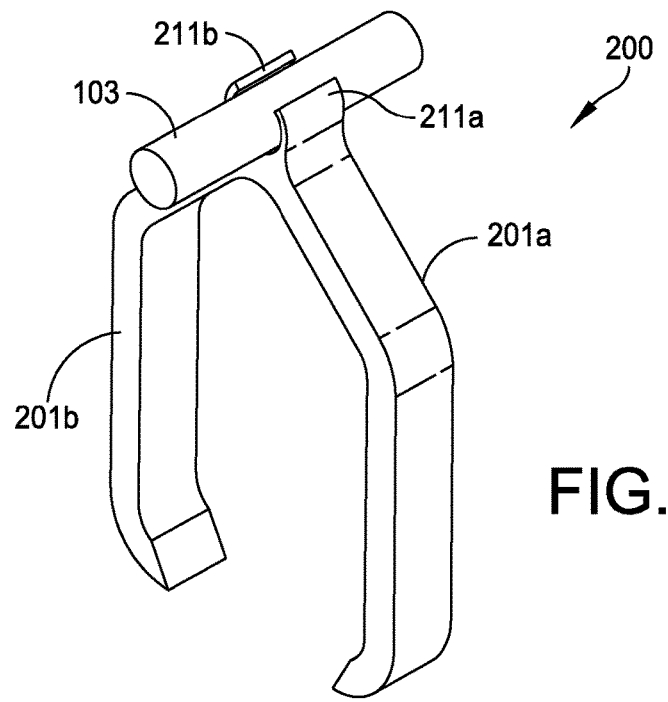
FIG. 13A
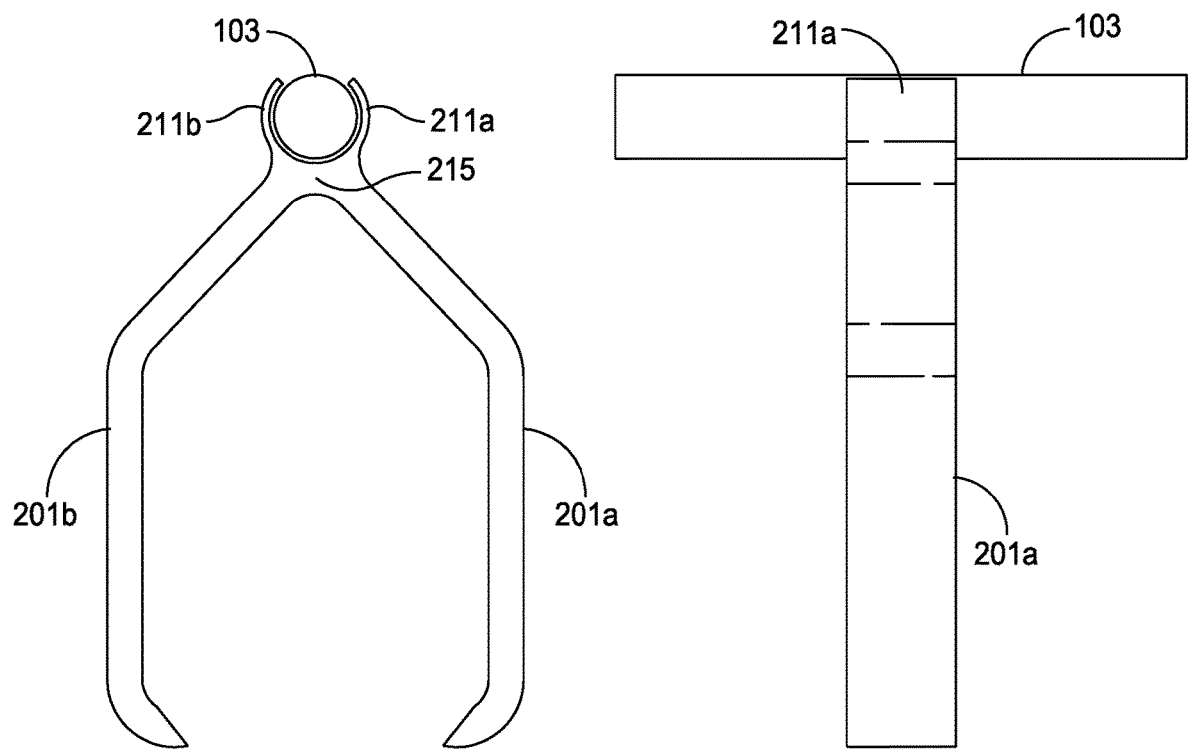
FIG. 13B
FIG. 13C

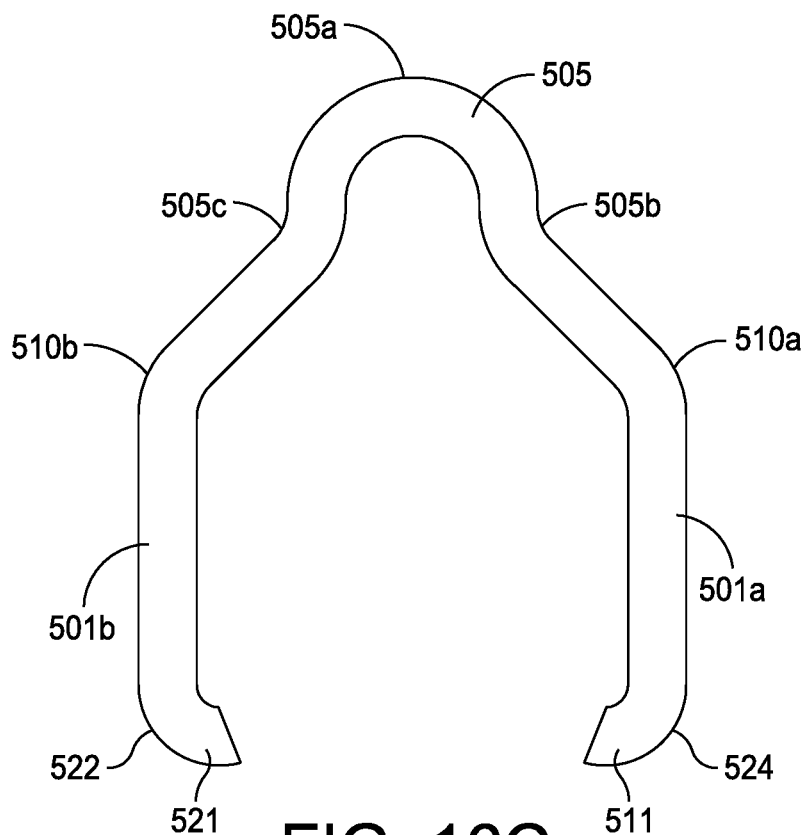
FIG. 16C
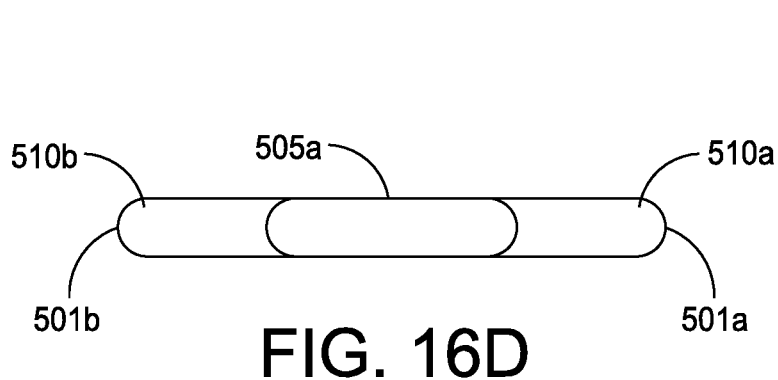
FIG. 16D
FIG. 16E
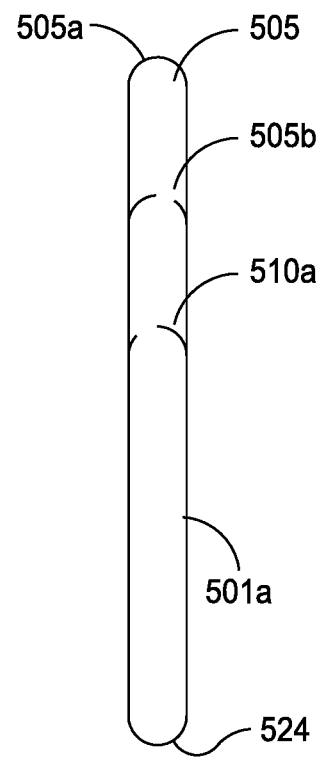
FIG. 16F

RADIOACTIVE THERAPEUTIC DEVICE

TECHNICAL FIELD

The present invention relates to the field of brachytherapy, which is the field of radiation treatment of cancerous or benign tissue that would occur in the body by placing radiation sources in or near the cancerous tissue.

The present invention is directed to permanent application of radiation sources and to methods of permanently affixing sources for permanent application.

BACKGROUND OF THE INVENTION

Ionizing radiation is employed in the management of a wide variety of malignant tumors, providing a mechanism whereby the malignancy can be destroyed while the normal tissues are preserved. With preservation of normal tissues, normal function and normal appearance may also be preserved. Hence, ionizing radiation forms part of the treatment for over half of all patients with cancer.

The overall effectiveness of radiation therapy, however, depends upon the balance between effective tumor control and morbidity due to the treatment. It is understood that the differential effects of ionizing radiation on tumors and normal tissues gives rise to a favorable therapeutic ratio for most patients. However, radiation can have destructive immediate and delayed effects on normal tissues. Techniques employed for radiation therapy significantly affect the incidence and severity of these destructive effects. The overall goal of radiation therapy is to maximize the effect of the radiation on tumor tissue while minimizing the effect of the radiation on normal tissue. Because the effect is generally proportional to the dose, this goal is generally accomplished by maximizing the dose to tumor tissue while minimizing the dose to normal tissue.

Various techniques have been developed to treat tumors in the body. In general, the use of radiation as a means to reduce or eliminate malignancy has been known for many years. One of the major issues in all of the techniques is the prevention of damage to healthy tissue. Because all types of ionizing radiation affect tissues by means of the same basic physical mechanisms, differences in spatial or temporal distributions are responsible for different effects observed. The method for delivering radiation thus becomes highly significant.

The type of radiation treatment of malignant tumors most often performed involves directing a beam of radiation from a point external to the patient's body onto the area of the body in which the tumor is located, for the purpose of shrinking and ultimately destroying the tumor. This technique is known as "teletherapy" or external beam radiation therapy. Such treatment exposes normal healthy tissue to a high dose of radiation in the beam and consequently subjects the normal tissue to potential injury. Conventional external beam radiation treatments rely on multiple fractions of dose in order to ensure that the highest fractions of tumor cells are exposed at the most sensitive parts of the cell life cycle.

In contrast to external beam radiation therapy, brachytherapy is a method of radiation treatment of cancerous tissue in which the radiation source is placed in or near the cancerous tissue. Because of the proximity of the radiation source to the target tumor or cancerous tissue, brachytherapy treatment permits administration of a higher radiation dose to the tumor with better sparing of surrounding normal healthy tissues.

Because a delivered dose from a radiation source decreases proportionately to the square of the distance from that source, brachytherapy permits the delivery of very high radiation doses to those areas of a tumor in close proximity to the source, with relative sparing of more distant tissues. With careful placement, so that the radiation source is in proximity to the tumor or target tissue and distant from normal tissue, effective therapy against the tumor may be combined with minimal collateral damage to normal tissues.

Brachytherapy came into use as a treatment tool for cancer soon after the discovery of radium by Marie Curie in 1898. Goldberg and London used it for the treatment of facial basal cell carcinomas in 1903 with surface applicators.

Brachytherapy can be applied to cancer either by permanent implantation or by temporary application of removable sources. Permanent implantation results in the radioactive source, or sources, being left in the body in perpetuity, delivering their radiation dose until the radioactive material in the source has completely decayed away. Temporary application results in the radioactive source, or sources, being left only temporarily in or near the body, delivering their radiation only until the radioactive source or sources are removed.

A variety of radionuclides and methods for permanent or temporary implantation have been developed. A variety of radioisotopes, including $^{125}$Iodine, $^{103}$Palladium, $^{198}$Gold, $^{131}$Cesium, $^{137}$Cesium, $^{60}$Cobalt, $^{169}$Ytterbium and $^{192}$Iridium, have been used in the treatment of cancers involving such tissues as the breast, the prostate, the brain, lung, the head and neck, the female reproductive tract (including cervix, vagina, endometrium), rectum, esophagus, bronchus, bile duct, skin, pancreas, the musculoskeletal system and related soft tissue sarcomas, and the eye.

Commonly, radioactive sealed sources, sometimes referred to as "seeds", employed in brachytherapy implants are intended for permanent implantation. A description of certain types of brachytherapy sources can be found in B H Heintz et al., "Comparison of I-125 sources used for permanent interstitial implants," Medical Physics, Vol. 28, No. 4, p. 673 (April 2001), the contents of which are hereby incorporated by reference. Certain devices known in the prior art are intended for insertion directly into the tissues without employing a needle or other similar delivery device. An example of such a device may be found in the disclosure of U.S. Pat. No. 4,815,449. This patent provides, in certain embodiments, an implant of sufficient rigidity to be driven into a tumor without deflection, so that the implant may be used independently of a positioning or delivery device.

Alternatively, brachytherapy sources may be positioned in the tissues to be treated by insertion through a delivery device, for instance, a needle. Using a delivery device may allow more precise positioning of brachytherapy sources in areas requiring treatment. Brachytherapy sources from various manufacturers may be made to the same set of specifications so that they are compatible with those delivery systems in common use. In those delivery systems, the brachytherapy sources may be preloaded into needles or other delivery devices. The position of a plurality of brachytherapy sources within the delivery device may be maintained by placing loose spacers between the brachytherapy sources to establish and maintain a desired positioning. Once the brachytherapy sources are positioned in the delivery device, insertion into the tissues takes place. To insert the brachytherapy sources, the needle containing them must first be inserted to a preselected depth into the appropriate position in the patient's tissues. An injection mechanism such as a mandrel may then be inserted into the needle with its distal end in contact with the brachytherapy sources. The needle, thereafter, may be withdrawn over the mandrel, leaving the brachytherapy sources and loose spacers resident in the preselected tissue area. Once positioned within the tissues using this method, the brachytherapy sources and loose spacers are free to move from their original position, as there are no constraints on the position or orientation of the brachytherapy sources. This can lead to the undesirable consequence that dose distribution within the tissue may be changed. For instance, movement of the brachytherapy sources after deployment can change the area being irradiated and can change the dose being delivered both to the preselected tumor regions and to the surrounding normal tissues.

There remains, therefore, a need for a system that can retain the brachytherapy sources in position relative to one another prior to delivery, and which can retain the position of the brachytherapy seeds in relation to the tumor after the seeds are delivered into the tissues.

Numerous approaches to solve this problem have been developed. In order to maintain the radioactive sources and spacers in their appropriate relative positions, devices have been designed to join these sources and spacers together. Examples of such devices are described in U.S. Pat. No. 6,709,381 to Munro, U.S. Pat. No. 6,820,318 to Terwilliger et al. and U.S. Pat. No. 6,010,446 to Grimm, which are all incorporated herein by reference. These devices preserve the relative linear positioning of the multiple sources but provide only limited resistance to longitudinal movement.

A number of approaches have been utilized to prevent further displacement of the sources. Examples include U.S. Pat. No. 8,114,007 to Lamoureux et al. and U.S. Pat. No. 8,366,598 to Lamoureux et al., which are incorporated herein by reference, which describe a source or sources molded within a polymeric material to encapsulate the radioactive sources and includes a plurality of protrusions on the outer surface of the encapsulating polymeric material to resist migration and rotation.

Another example is U.S. Pat. No. 4,936,823 to Colvin et al., which is incorporated herein by reference, which describes resilient arms which can be manipulated to anchor a body containing a radioactive source within a body canal. Further, U.S. Pat. No. 6,264,599 to Slater et al., which is incorporated herein by reference, describes a method similar to Colvin '823 except that Slater '599 provides for automatically positively engaging the resilient arms into the tissue.

All of these methods require substantial tissue surrounding the sources to prevent lateral movement and to provide resistance to the deployment of the resilient arms or the protrusions of the polymeric extrusions. Although these methods are, in many cases, sufficient when placing the brachytherapy source into massive tumor or tumor tissue itself surrounded by healthy tissue, there exist cases where treatment is desired after surgical removal/resection of the tumor.

Gross surgical removal of tumor tissue can leave behind traces of tumor, precancerous, or other diseased tissue which can foster recurrence or metastasis of the tumor. Accordingly, the site of removal of a tumor is often treated postoperatively in an attempt to destroy any such diseased tissue left behind by the surgery. Conventional techniques for treating the site of surgical removal of a tumor include post-operative administration of radiation, chemotherapy, and/or heat.

Although external beam therapy and short-range therapy are two commonly practiced techniques for administration of post-operative radiation, external beam is less desirable. In external beam therapy, also known as teletherapy, an external radiation beam is directed at the treatment site. In teletherapy, the radiation beam must be carefully positioned with respect to the treatment site to minimize the radiation exposure of the surrounding healthy tissue. Even with a high degree of precision, however, healthy tissue in the vicinity of the treatment site may receive significant doses of radiation. This side effect can be compounded when treatment requires repeated administrations, each requiring careful positioning of the radiation beam.

In short-range brachytherapy, radioactive sources are placed at or near the treatment site, i.e. the region adjacent to the surgical resection, to provide site-specific delivery of radiation therapy, potentially reducing undesirable side effects associated with teletherapy, such as irradiation of healthy tissue. One common brachytherapy technique uses catheters to deliver temporary radiation to the treatment site. In this technique, numerous catheters may be simultaneously inserted into or around the treatment site, sewn into place, loaded with solid isotopic pellets for a prescribed time, and then removed. The process of placing a number of catheters simultaneously within the appropriate region is cumbersome and time intensive. Additionally, invasive insertion and external exposure of the catheters presents an increased risk of infection to the patient and can result in significant discomfort for the patient during treatment. Finally, any subsequent treatment, for example, treatment following tumor recurrence, requires that the entire process be repeated from the beginning. For these reasons, temporary brachytherapy is not a desirable treatment method.

A common brachytherapy technique employs radioactive implants to deliver permanent radiation therapy. In this technique, numerous radioactive sources are implanted directly into or around the treatment site. However, as the tumor, in these cases, has already been surgically removed and the desired treatment is to the limited amount of tissue adjacent to the surgical resection, there is insufficient tissue in the region of the target to employ the methods described above, namely relying on the pressure of the surrounding tissue to render the irregular surface to be immobile, as described by Munro '381, Terwilliger '318, Grimm '446, Lamoureux '007, or Lamoureux '598, or to provide tissue around the source in all directions to provide means for resilient arms to engage, as described by Colvin '823 or Slater '599.

In limited cases, a device for providing radiation treatment to a treatment site that can be implanted at the time of tumor removal and which delivers a relatively uniform dose of radiation throughout the surrounding tissue as described by U.S. Pat. No. 6,527,693 to Munro et al., which is incorporated herein by reference. However, in many cases, such as the lung, the residual tissue remaining after resection and requiring treatment is irregularly shaped and cannot be treated using the method described by Munro '693.

Methods to affect this type of treatment have been described. Reference is made to W. Lee et al., "Limited resection for non-small cell lung cancer: observed local control with implantation of 125I brachytherapy seeds," Annals of Thoracic Surgery 75(1), January 2003, pp. 237-242, which is incorporated herein by reference, in which is described a brachytherapy technique that uses strands of ten $^{125}$Iodine seeds, embedded in polyglactin 910 suture with 1 cm spacing which were affixed by suture along the resection margin or 0.5 cm on either side of the margin. Reference is also made to A. Chen et al., "Intraoperative 125I brachytherapy for high-risk stage I non-small cell lung carcinoma," Int. J. Radiation Oncology Biol. Phys., Vol. 44, No. 5, 1999, pp. 1057-1063, which is incorporated herein by reference, in which is described an alternative method utilizing vicryl surgical mesh imbedded with stranded 125Iodine radioactive seeds placed over the tumor bed and surgical resection line and sutured in place. Both of these methods require manual suturing of the strands or mesh in place. The difficulty of precisely delivering the brachytherapy sources intraoperatively to achieve the proper dose distribution and minimizing the radiation dose to the clinicians performing the procedure make these techniques less desirable.

Alternative methods of attaching brachytherapy sources to tissue is described by Munro et al. in U.S. Pat. No. 10,286,227 using a barbed protrusion fabricated from shape memory alloy. This provides a method of attachment without firmly fixing the position of the source, thereby allowing source movement causing changes to the dose distribution.

An improved method for delivering a brachytherapy source has been described in U.S. Pat. Nos. 7,604,586, 7,972,260, 8,267,849, and 9,763,660, all to Wazer et al., which are incorporated herein by reference, in which the radioactive sources are incorporated directly into a subset of the surgical staples used in the procedure. In this way, the sources are secured in position directly adjacent to the surgical resection and are immobile. This method facilitates the precise placement of brachytherapy sources relative to the surgical margin, assures the seeds remain fixed in their precise position for the duration of the treatment, overcomes the technical difficulties of manipulating the seeds through the narrow surgical incision, and reduces the radiation dose to the clinicians. However, this method also has a number of drawbacks.

In particular, the concept of delivering the radioactive sources temporally and spatially adjacent to the surgical resection is of limited value. In practice, most procedures remove the suspected tumor tissue (and therefore remove the surgical stapling/resection device) and await pathological analysis before deciding to perform brachytherapy. Physicians do not want to introduce brachytherapy sources into the patient until it has been determined that the tissue is malignant. Therefore, the advantage of having the brachytherapy source delivery device physically aligned with the surgical stapling/resection device is lost.

The attachment of a brachytherapy source delivery device to the surgical resection device/stapler also has several other disadvantages. It provides a more cumbersome device for the surgeon to manipulate and may introduce difficulties introducing the assembly through standard thoroscopic ports. It can also interfere with surrounding tissue, leaving less margin around the suspect tumor from which to excise. There is also risk that the brachytherapy source delivery device could dislodge from the surgical resection device/stapler, thereby complicating the procedure.

The use of staple-like brachytherapy sources requires access to both sides of the tissue through which the source will be deployed. The staple-like brachytherapy sources are pushed through the tissue from one side and an anvil-like element is positioned on the opposite side to affect the bending and securing of the source. The amount of tissue between the two elements must be within a very narrow limited range in order for the staple-like brachytherapy sources to be properly bent and secured. If the tissue is too thick, or the anvil-like element does not assume the proper spacing, the staple-like brachytherapy sources can be incorrectly deformed and not secured, leaving them loose to move about the patient. This can also be a concern if there are areas where no tissue exists between the two elements of the brachytherapy delivery device. This will leave sources free-floating within the patient.

Accordingly, there remains a need for a system that can easily deploy and retain the brachytherapy sources in the desired treatment position adjacent to a surgical resection that alleviates the problems associated with the above-delineated systems.

SUMMARY OF THE INVENTION

Described herein is a brachytherapy source delivery device including a first tissue-piercing leg having proximal and distal ends, a second tissue-piercing leg having proximal and distal ends, wherein the proximal ends of the first and second tissue-piercing legs are joined at a span section in a first angular orientation with respect to each other, and a carrier element formed at, or attached to, the span section, the carrier element configured to support a radioactive brachytherapy source. The distal ends of the first and second legs can be curved inward toward each other to pierce a tissue when engaged toward each other into a closed position. The first and second tissue-piercing legs can be formed of a wire having a circular cross-sectional shape. The first and second tissue-piercing legs can be formed of a wire having a non-circular cross-sectional shape. The carrier element can be formed as part of a unitary structure with the first and second tissue-piercing legs. The carrier element can be a tube having a circular or non-circular cross-sectional shape. The carrier element can extend along a full length of the radioactive brachytherapy source. The carrier element can have an opening at a top portion of the carrier element. The brachytherapy source delivery device can further include a radiation shield disposed on the carrier element. The carrier element is tangentially attached to the span section. In the brachytherapy source delivery device, each of the first and second tissue-piercing legs can have a length that is greater than a length of the span section. The length of each of the first and second tissue-piercing legs can be at least two times the length of the span section. The span section can define a first curved exterior surface having an angle of approximately 90 degrees, a distal end of the first leg can form a second curved exterior surface having a second angle of approximately 90 degrees, and a distal end of the second leg can form a third curved exterior surface having a third angle of approximately 90 degrees. The legs can be brought into the closed position from an open position in a single, continuous motion.

A brachytherapy source delivery device can include a one piece wire member that extends in a substantial single plane, said wire member including a pair of longitudinally extending legs that each have a tissue piercing distal end, and an interconnecting span section that connects proximal ends of the respective pair of longitudinally extending legs, and a carrier element that attached to the span section and that is configured to receive a radioactive brachytherapy source. The tissue piercing distal ends of the respective longitudinally extending legs can each be formed as a barb, and the respective barbs can extend in a direction toward each other. The carrier element can be a tubular member into which the radioactive brachytherapy source is received. The tubular member can extend longitudinally along a longitudinal axis that is disposed at an angle to the single plane of the wire member. The span section can be arcuate and configured to continuously connect with the respective longitudinally extending legs that are of equal length so as to form a symmetric wire member. The longitudinal axis of the tubular member can be disposed at substantially at a right angle to the single plane of the wire member. The longitudinal axis of the tubular member can be disposed within the single plane of the wire member. The tubular member can extend longitudinally along a longitudinal axis, and the longitudinal axis of the tubular member can either be at an acute or right angle to the single plane of the wire member.

A method includes providing a brachytherapy source delivery device including first and second tissue-piercing legs each having proximal and distal ends, wherein the proximal ends of the first and second tissue-piercing legs are joined at a span section in a first angular orientation with respect to each other, and a carrier element formed at, or attached to, the span section, the carrier element configured to support a radioactive brachytherapy source, and joining the first and second tissue-piercing legs together to pierce a tissue site in a single motion bringing the brachytherapy source delivery device from an open position to a closed position. The method can also include attaching a brachytherapy source to the carrier element prior to joining the first and second legs together

BRIEF DESCRIPTION OF THE DRAWINGS

It should be understood that the drawings are provided for the purpose of illustration only and are not intended to define the limits of the disclosure. In the drawings depicting the present invention, all dimensions are to scale. The foregoing and other objects and advantages of the embodiments described herein will become apparent with reference to the following detailed description when taken in conjunction with the accompanying drawings in which:

FIG. 9A is a perspective view of the carrier element and brachytherapy source approximately parallel to the plane of the wire form;

FIG. 9B is a front view of the device of FIG. 9A;

FIG. 9C is a side view of the device of FIG. 9A;

FIG. 10A is a perspective view of an axis of the carrier element and source at a predetermined angle with respect to the plane of the wire form;

FIG. 10B is a front view of the device of FIG. 10A;

FIG. 10C is a side view of the device of FIG. 10A;

FIG. 13A shows a perspective view of a device having a generally rectangular cross-sectional shape;

FIG. 13B shows a front view of the device of FIG. 13A;

FIG. 13C shows a side view of the device of FIG. 13A;

FIG. 16C is a front view of the device of FIG. 16A without the course attached;

FIG. 16D is a top view of the device of FIG. 16A;

FIG. 16E is a bottom view of the device of FIG. 16A;

FIG. 16F is a side view of the device of FIG. 16A;

DETAILED DESCRIPTION

The present invention provides a means for achieving greater ability to attach and firmly affix a brachytherapy source to a desired tissue site. The desired tissue site refers to the tissue that is intended to receive a brachytherapy treatment by a brachytherapy radiation source. The device is a formed wire used to support a radioactive brachytherapy source and to be deployed by pressing the legs of the device toward each other, piercing the tissue between them and securing the device to the tissue in a single, continuous motion which may be referred to herein as a "single step".

In an example embodiment shown in FIGS. 1A-1E, the device 100 is a wire formed to include first and second tissue-piercing legs 101a, 101b with a carrier tube 102 attached to the formed wire. The first and second tissue-piercing legs 101a, 101b may be more generally referred to as a "wire form" or "formed wire" herein. In use, the carrier tube 102, which may be referred to as a "carrier element" is configured to hold a radioactive brachytherapy source (i.e., source 103 shown in FIGS. 2A-2C for example). The legs 101a, 101b are formed of a wire having a circular cross-sectional shape in this embodiment. Other non-circular cross-sectional shapes (such as rectangular, square, or hexagonal) can be implemented within ordinary skill. Refer, for example, to FIGS. 13a-15 for various cross-sectional shapes.

Figure 1A:
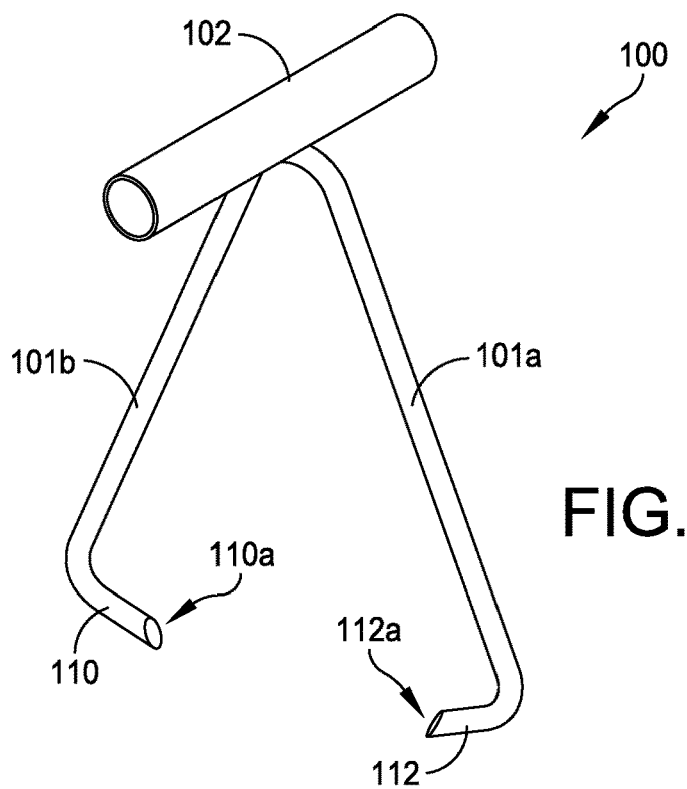
FIG. 1A is a perspective view of a brachytherapy source delivery device having tissue-piercing legs and a carrier element.

FIG. 1A is a perspective view of the device 100 including tissue-piercing legs 101a, 101b and carrier element 102. As shown in FIG. 1A, the brachytherapy source delivery device 100 includes a first tissue-piercing leg 101a having proximal and distal ends, and a second tissue-piercing leg 101b likewise having proximal and distal ends. An arm 110 extends from the distal end of the second tissue-piercing leg 101b and an arm 112 extends from the distal end of the first tissue-piercing leg 101a. Each arm 110, 112 has a respective barb 110a, 112a extending therefrom and the barbs 110a, 112a are in an orientation such that the ends of the barbs 110a, 112a are facing each other.

The carrier tube 102 is attached to the proximal ends of the first and second tissue-piercing legs 101a, 101b. The carrier tube 102 can be welded to the wire form. Other attachment mans can be implemented, such as adhesives (e.g., cyanoacrylate, glue, or epoxy), especially with polymers, welded polymers, or biocompatible soldering techniques.

Figure 1B:
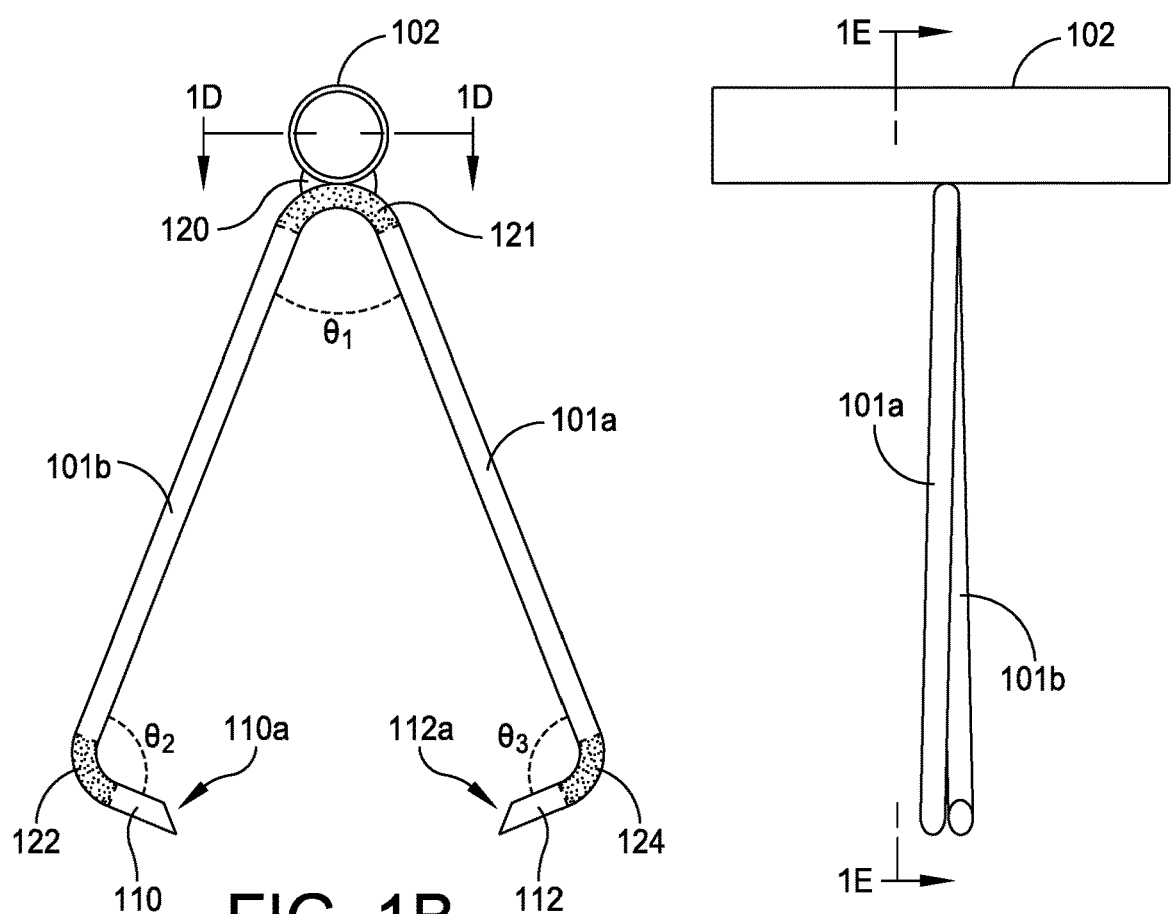
FIG. 1B is a front view of the brachytherapy source delivery device of FIG. 1A.

FIG. 1B is a front view of the device 100. As shown in FIG. 1B, the proximal ends of the first and second legs 101a, 101b are joined at a span section 121 in a first angular orientation with respect to each other. The span section can be arcuate and configured to continuously connect with the respective longitudinally extending legs that are of equal length so as to form a symmetric wire member. The span section 121 is generally denoted by the dotted-line section 121 indicating the curved portion where the proximal ends of the legs 101a, 101b are joined. This angular orientation is shown by angle $\theta_1$ which may be approximately 15-90 degrees. In an alternate embodiment of the invention this angle may be on the order of 15-120 degrees. This angle needs to be sufficient to "open" the barbs to allow them to extend beyond a resting open position (as shown in FIG. 1B) and go around the desired tissue site, yet not too large so that the force in deploying the brachytherapy source delivery device 100 is able to overcome the force provided by the angular orientation of the first and second tissue-piercing legs 101a, 101b.

Each tissue-piercing leg 101a, 101b has a respective arm 112, 110 extending from a distal end of the leg 101a, 101b, which may be joined at a respective curved section 124, 122. The curved section 122 may have an angle $\theta_2$ of approximately 60-90 degrees. Likewise, the curved section 124 may have an angle $\theta_3$ of approximately 60-90 degrees. The angle is preferably approximately 90-degrees to facilitate the piercing of the tissue to which the formed wire is to be applied. An angle less than 90-degrees would also work but likely not as effectively at piercing tissue. In some embodiments $\theta_1$, $\theta_2$, and $\theta_3$ can all have the same value of approximately 90-degrees.

Although the arms 110, 112 are shown as being substantially straight, there may be a bend along this segment to further assist in securing the device 100 to an underlying tissue site. Likewise, the ends of the barbs 110a, 112a may have varying shapes, for example as shown in FIGS. 17A-17D herein.

The carrier tube 102 is attached tangentially with respect to the span section 121 of the joined tissue-piercing legs 101a, 101b. By tangentially, it is intended to mean herein that the carrier tube 102 is an approximately straight line or plane that touches a curve or curved surface (the span section) at a point. Note that by tangentially securing the carrier tube to the tissue-piercing legs, this can also reduce or even eliminate attenuation that could result if the carrier tube were placed along the length of a metal leg. A metallic wire that is, for example, placed along the entire length of the radioactive source attenuates the radiation from the entire length of the source. Thus, a tangentially connected source, such as that disclosed according to the present disclosure, does not have the attenuation along the entire length of the source, given that there is only contact at most at one point along the curve.

The length of each of the legs 101a, 101b is longer than a length of the span section 121 such that a sufficient force applied to the legs causes the tissue to be pierced while providing the sufficient pivot by the span section. For example, the length of the legs 101a, 101b can be at least two times the length of the span section, as shown in FIG. 1B. Other ratios and variations in the length of the legs with respect to the span section will be apparent in light of the present disclosure.

Figure 1C:
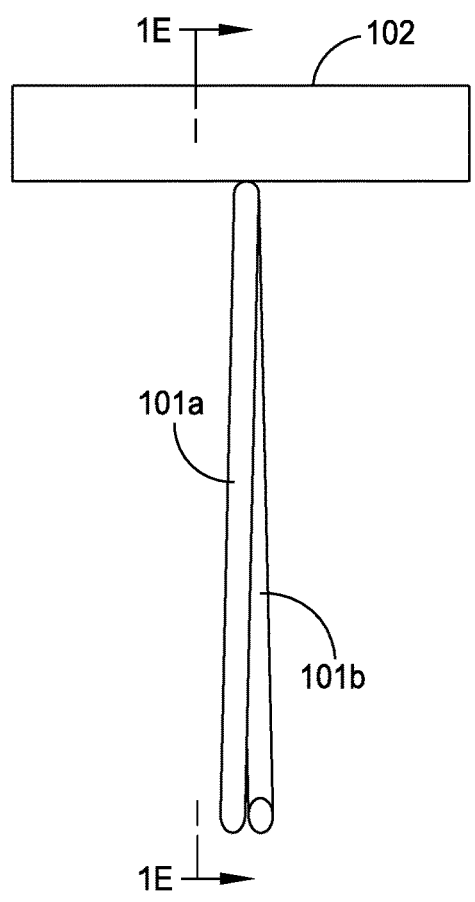
FIG. 1C is a side view of the brachytherapy source delivery device of FIG. 1A.

FIG. 1C is a side view of the brachytherapy source delivery device 100, showing the carrier element 102 tangentially attached to the tissue-piercing legs 101a, 101b. Note that there is an offset in the distal ends of the legs 101a, 101b so that they are next to each other (i.e., side-by-side) as shown in FIG. 1C. However, in some embodiments, it will be appreciated that there can be no offset such that the legs 101a, 101b are along a same plane. This depends upon the desired tissue-piercing effect, whereas an offset is provided when desired to have the barbs of the legs next to each other (side-by-side) when in the closed position, and no offset is provided so that the barbs face each other (along a same plane) when in the closed position.

Figure 1D:
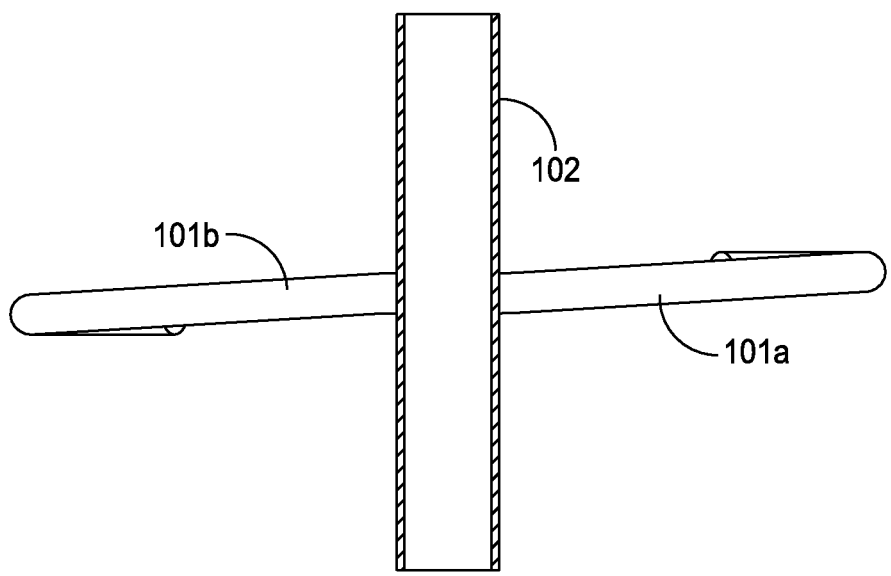
FIG. 1D is a cross-sectional view as taken through line 1D-1D of FIG. 1B.

FIG. 1D is a cross-sectional view as taken through line 1D-1D of FIG. 1B. As shown, there is an offset in that the legs 101a, 101b are at a slight angle with respect to the perpendicular axis of the carrier element 102. Thus, when pierced through a tissue, the barbs at the distal ends of the legs 101a, 101b will be side-by-side, for example as shown in FIG. 3C. The carrier element 102 is shown in semicircular cross-sectional shape in this view.

Figure 1E:
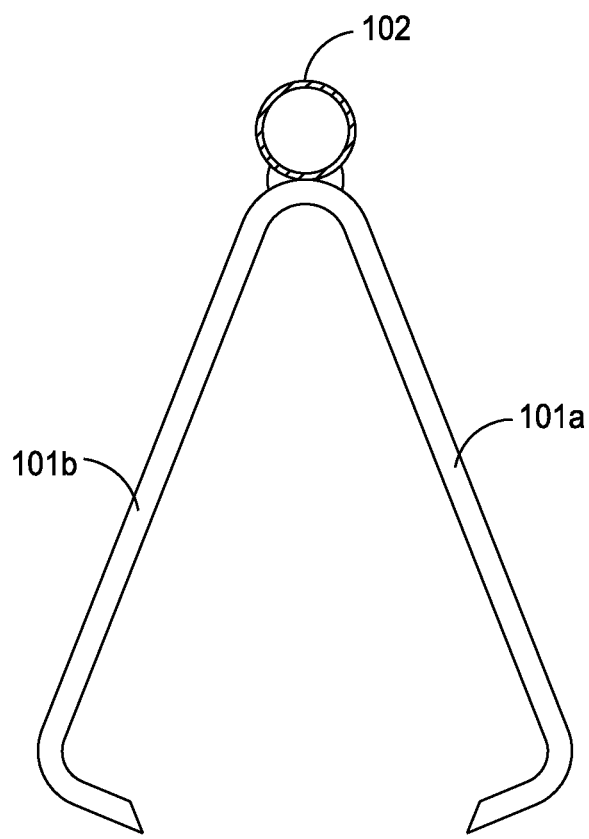
FIG. 1E is a cross-sectional view as taken through line 1E-1E of FIG. 1C.

FIG. 1E is a cross-sectional view as taken through line 1E-1E of FIG. 1C. The carrier element 102 is shown tangentially attached to the proximal ends of the legs 101a, 101b.

Figure 1F:
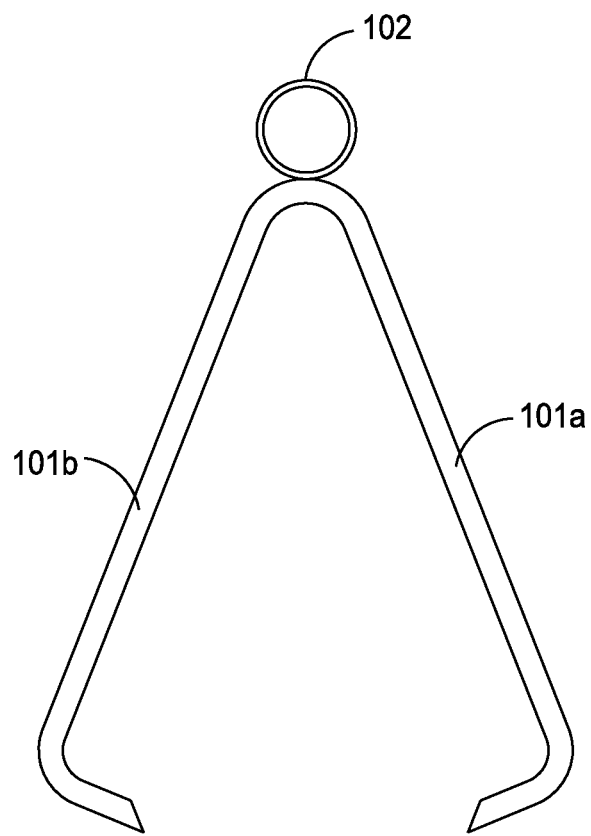
FIG. 1F is a front view of the device of FIG. 1A.
Figure 1G:
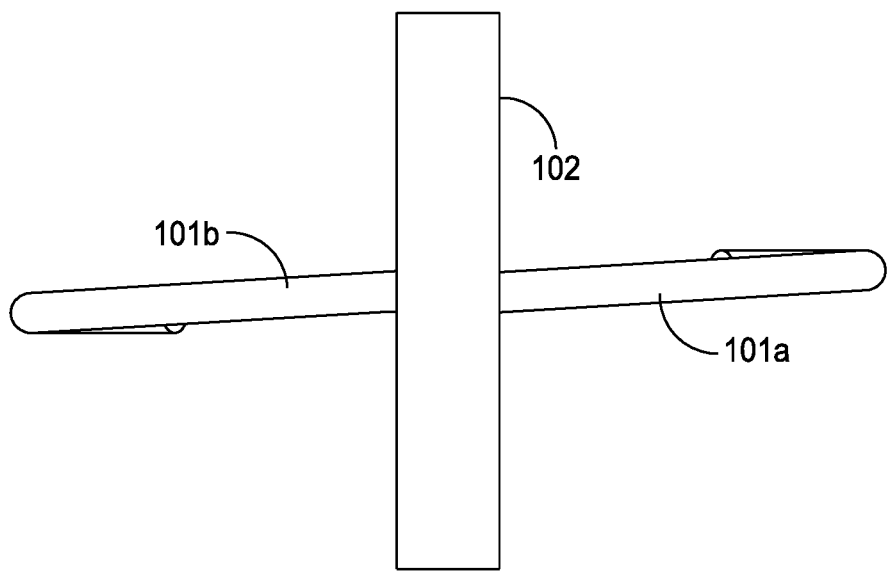
FIG. 1G is a top view of the device of FIG. 1A.
Figure 1H:
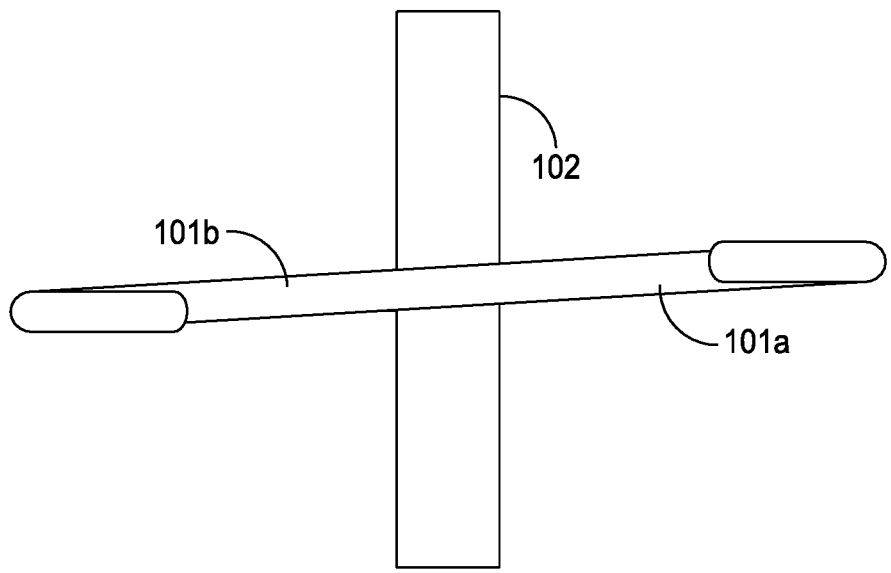
FIG. 1H is a bottom view of the device of FIG. 1A.

FIG. 1F is a front view of the device of FIG. 1A. FIG. 1G is a top view of the device of FIG. 1A. FIG. 1H is a bottom view of the device of FIG. 1A.

Figure 2A:
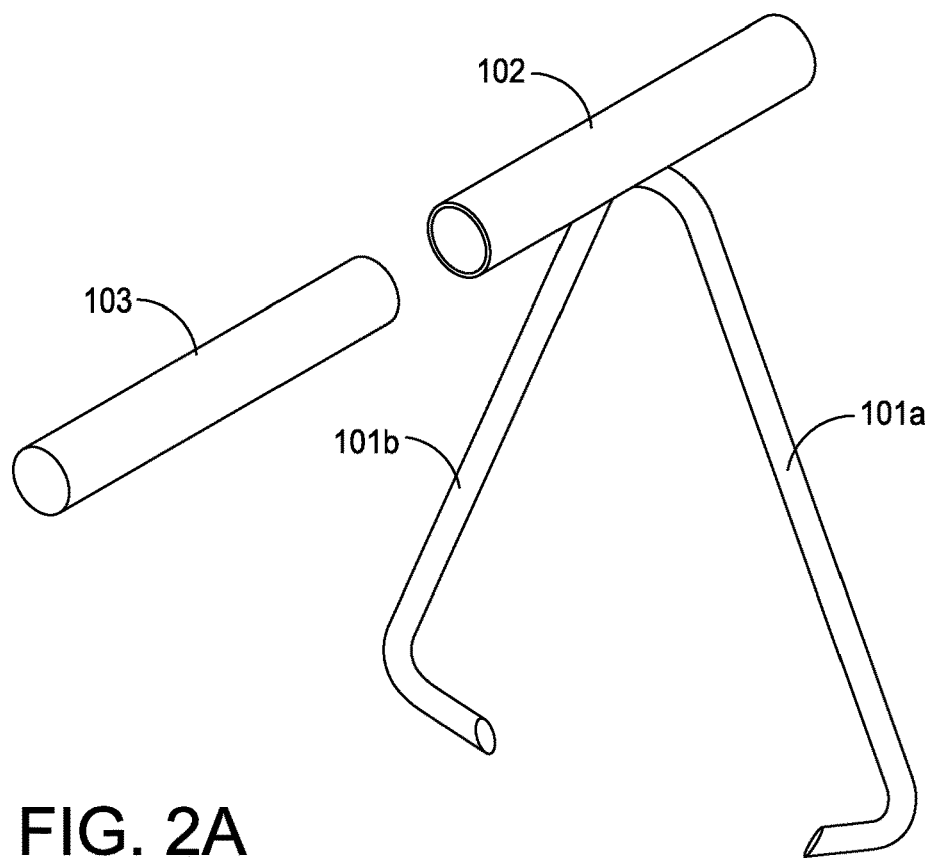
FIG. 2A is a perspective view of a brachytherapy source delivery device with the source prior to installment into the carrier element.
Figure 2B:
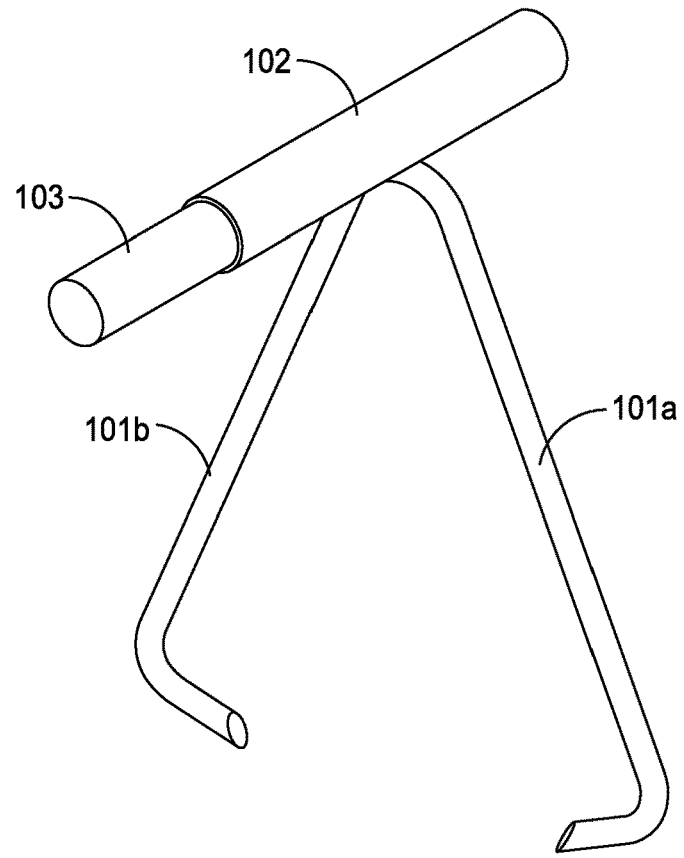
FIG. 2B is a perspective view of the brachytherapy source delivery device with the source partially installed in the carrier element.
Figure 2C:
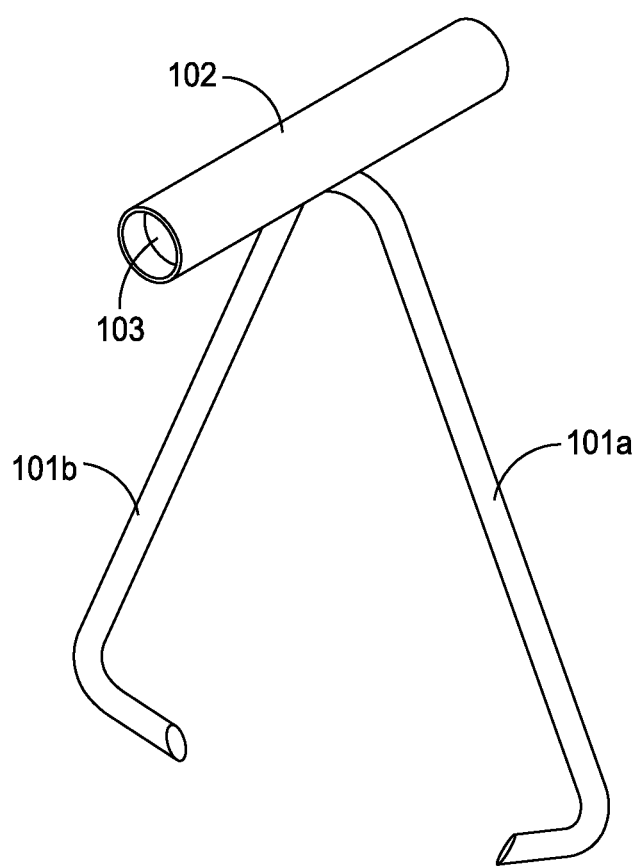
FIG. 2C is a perspective view of the source fully installed within the carrier element of the brachytherapy delivery device

Reference is now made to FIGS. 2A-2C, showing the source at various positions with respect to the carrier element. In use, a brachytherapy source 103 would be installed within the carrier tube 102 prior to deployment of the device 100. The source 103 is shown exterior of the carrier tube 102 in FIG. 2A, prior to installment of the source within the tube. FIG. 2B illustrates the source 103 partially installed within the carrier element 102, as being slid or otherwise placed within the tube. FIG. 2C illustrates the source 103 fully installed within the carrier element 102. As shown in FIG. 2C, the carrier element 102 extends along a full length of the radioactive brachytherapy source 103.

As shown, the carrier element 102 could remain open on both ends. The source 103 can be secured within the carrier element with an adhesive (such as cyanoacrylate). The source can be secured by deforming the carrier element 102 (e.g., forming a dent in the tube prior to inserting the source provides sufficient friction) or a dent after inserting likewise provides the requisite friction. Both ends of the carrier element 102 can be crimped to secure the source in place. The carrier element could be partially or completely sealed to leave the opening smaller than the source preventing its release.

Figure 3A:
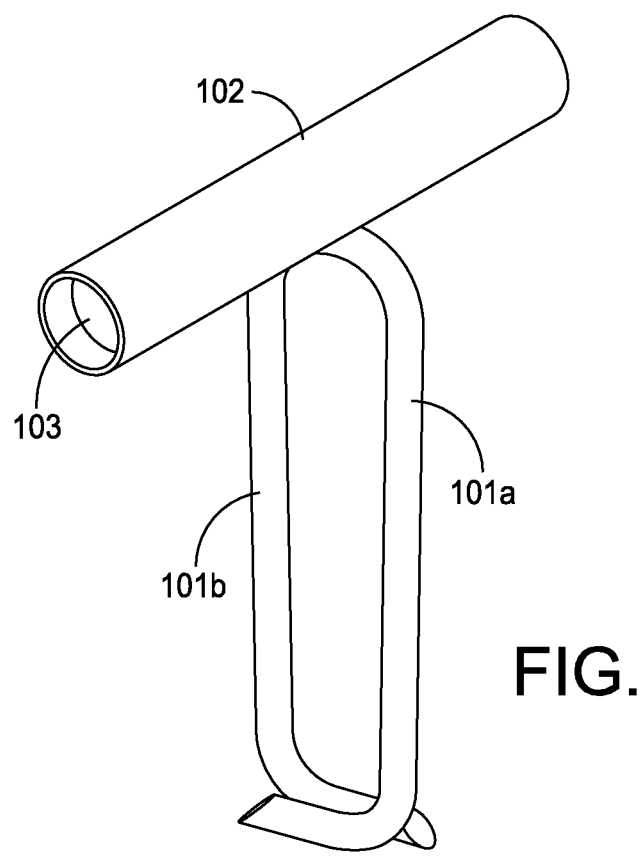
FIG. 3A is a perspective view of the brachytherapy source delivery device shown in the closed position.
Figure 3B:
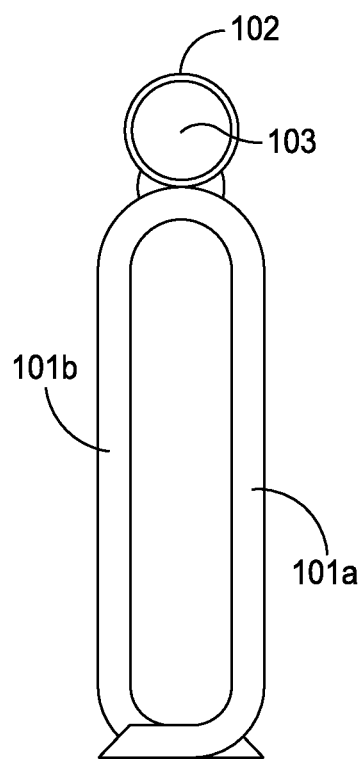
FIG. 3B is a front view of the device shown in the closed position with the legs piercing a desired tissue site.
Figure 3C:
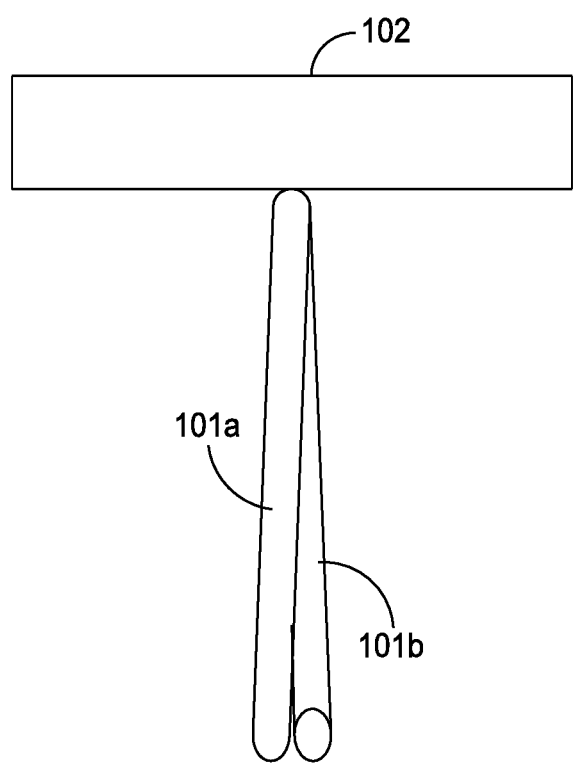
FIG. 3C is a side view of the device shown in the closed position with the legs piercing a desired tissue site.

As shown in FIGS. 3A-3C, at deployment, the legs of the wire form are placed over a segment of tissue and the legs are pressed together, causing the ends to pierce the tissue (not shown) and to secure the device 100 in place. FIG. 3A is a perspective view of the device 100 shown in the closed position. Although the desired tissue site is not shown, in the closed position the barbs pierce the underlying tissue. The barbs are shown side-by-side in the closed orientation; however, it will be appreciated that the barbs can face each other in the closed orientation. FIG. 3B is a front view of the device 100 shown in the closed position with the legs 101a, 101b piercing a desired tissue site. FIG. 3C is a side view of the device 100 shown in the closed position with the legs 101a, 101b piercing a desired tissue site.

Figure 4A:
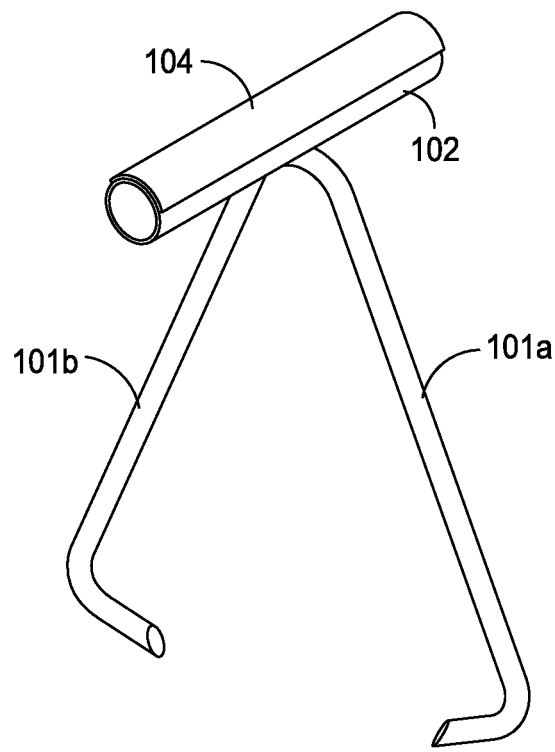
FIG. 4A shows a perspective view of the carrier tube with radiation shield.
Figure 4B:
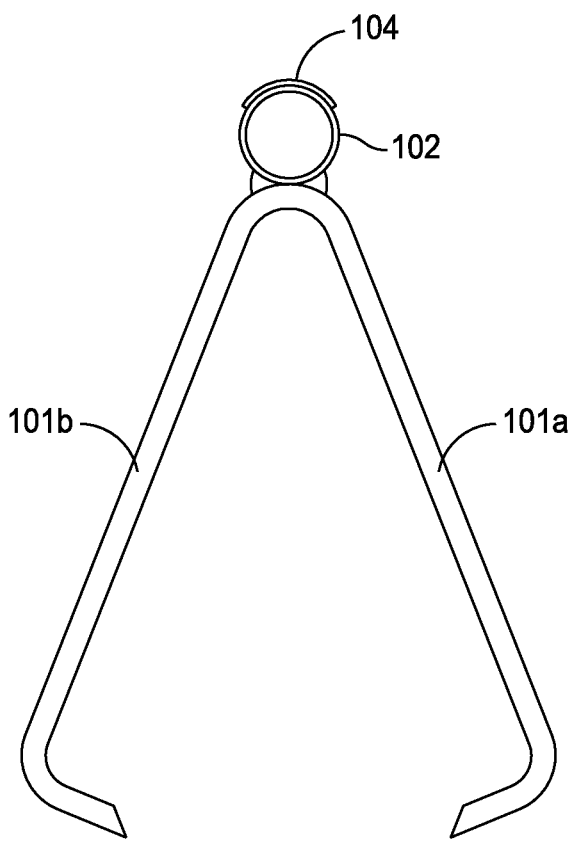
FIG. 4B is a front view of the carrier tube and radiation shield tangentially attached to the proximal ends of the legs.
Figure 4C:
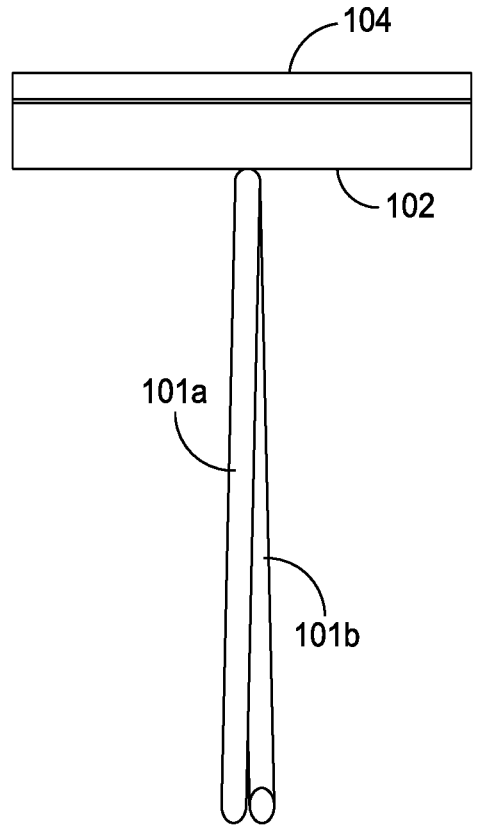
FIG. 4C is a side view of the carrier tube and radiation shield tangentially attached to the proximal ends of the legs.

In some embodiments, as shown in FIGS. 4A-4C, a thin radiation shield 104 can be attached to a section of the outer surface of the carrier tube 102 to reduce the radiation exposure in unwanted directions. FIG. 4A shows a perspective view of the carrier tube 102 with radiation shield 104. FIG. 4B is a front view of the carrier tube 102 and radiation shield 104 tangentially attached to the proximal ends of the legs 101a, 101b. FIG. 4C is a side view of the carrier tube 102 and radiation shield 104 tangentially attached to the proximal ends of the legs 101a, 101b. The radiation shield 104 can be any high-density biocompatible metal, such as gold, platinum, iridium, silver, or tungsten. The radiation shield 104 could also be a high-density metal such as lead if encapsulated in a biocompatible covering or coating.

Figure 5A:
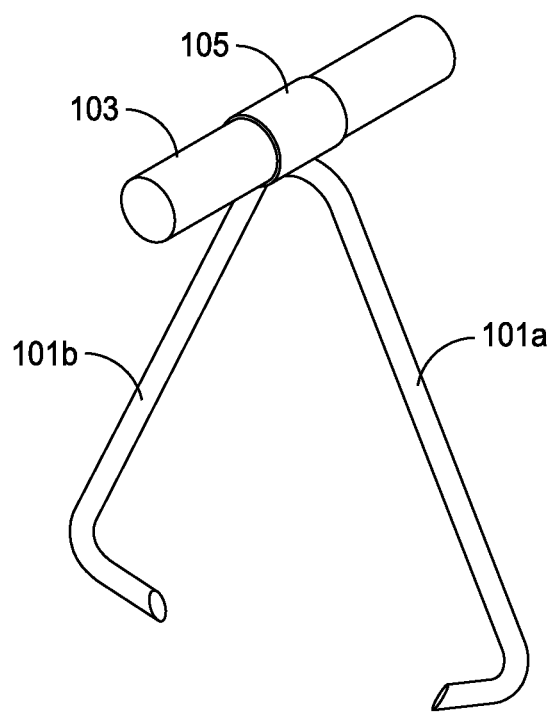
FIG. 5A is a perspective view of the shorter tube supporting the source.
Figure 5B:
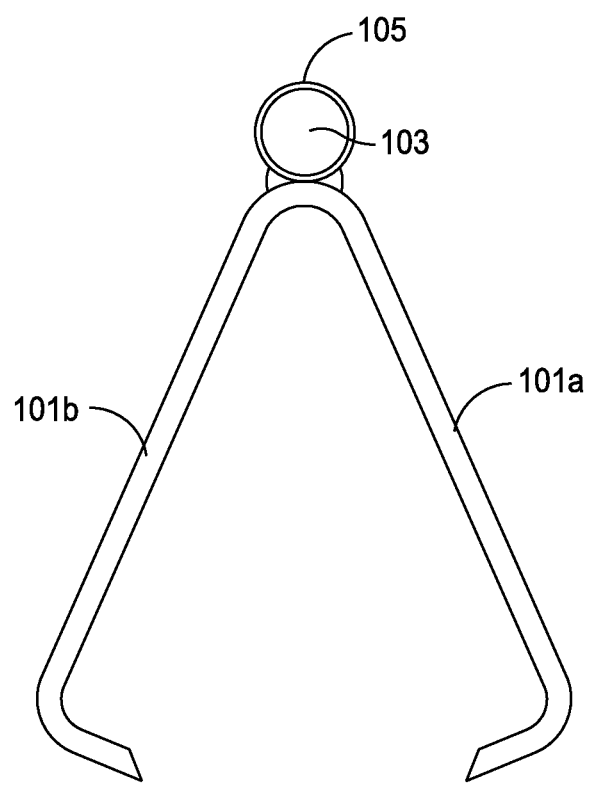
FIG. 5B is a front view of the device of FIG. 5A.
Figure 5C:
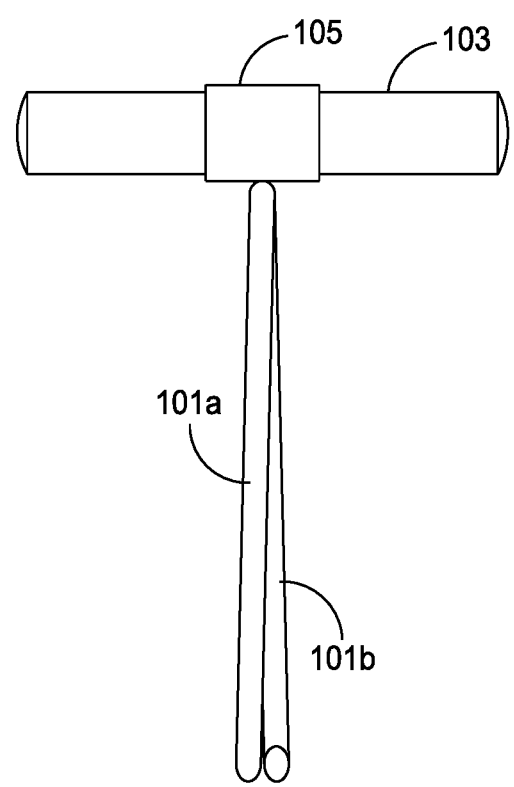
FIG. 5C is a side view of the device of FIG. 5A.

In another embodiment, the carrier tube does not need to encompass the entire length of the brachytherapy source. As shown in FIGS. 5A-5C, a shorter tube 105 could be used to carry the brachytherapy source 103. FIG. 5A is a perspective view of the shorter tube 105 supporting the source 103. FIG. 5B is a front view of the shorter tube 105 supporting the source 103, with the tube 105 tangentially attached to the proximal ends of the legs 101a, 101b via attachment member 120. FIG. 5C is a side view of the shorter tube 105 supporting the source 103, with the tube 105 tangentially attached to the proximal ends of the legs 101a, 101b.

Figure 6A:
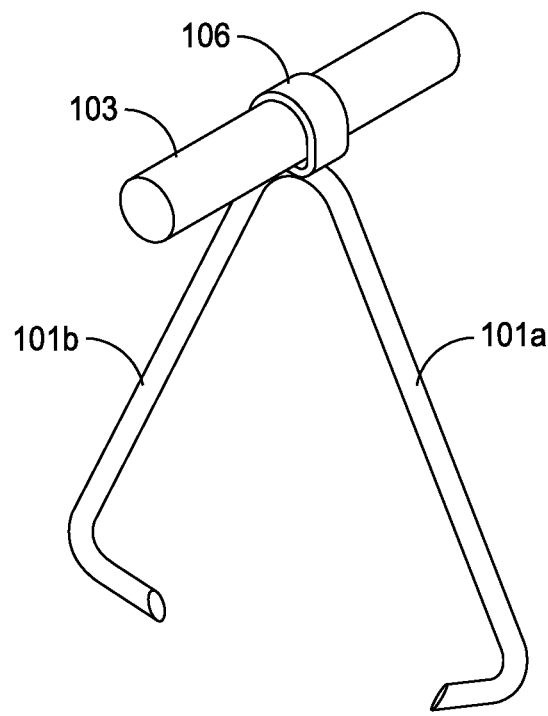
FIG. 6A is a perspective view of the device with a non-circular shaped element encircling brachytherapy radiation source.
Figure 6B:
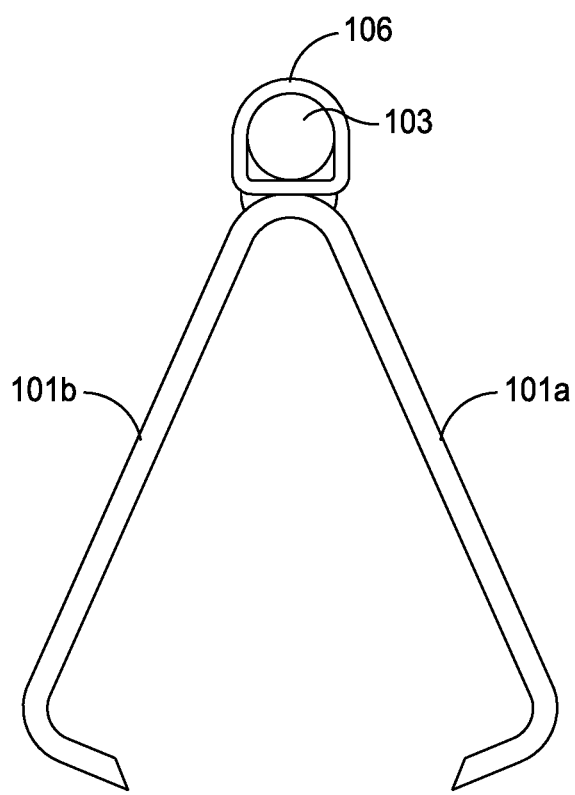
FIG. 6B is a front view of the device of FIG. 6A.
Figure 6C:
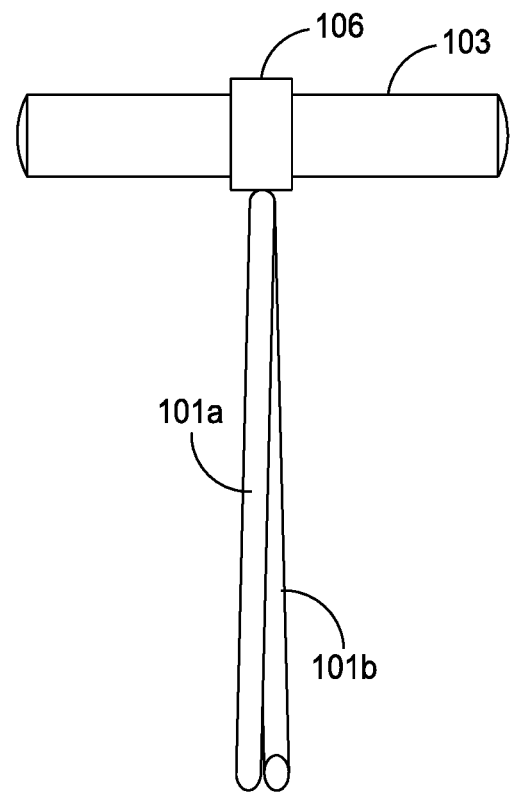
FIG. 6C is a side view of the device of FIG. 6A.

In another embodiment, the carrier element can be another non-circular shape that encircles the entire brachytherapy source can be used as shown in FIGS. 6A-6C. FIG. 6A is a perspective view of the device 100 with a non-circular shaped element 106 encircling brachytherapy radiation source 103. FIG. 6B is a front view of the element 106 encircling the source 103 at the proximal ends of the legs 101a, 101b. As shown, the element 106 has an approximate cross-sectional D-shape, with the flattened portion of the tube 106 tangentially attached to the span section connected at the proximal ends of the legs 101a, 101b. FIG. 6C is a side view of the tube 106 encircling the source 103 at proximal ends of the legs 101a, 101b.

Figure 7A:
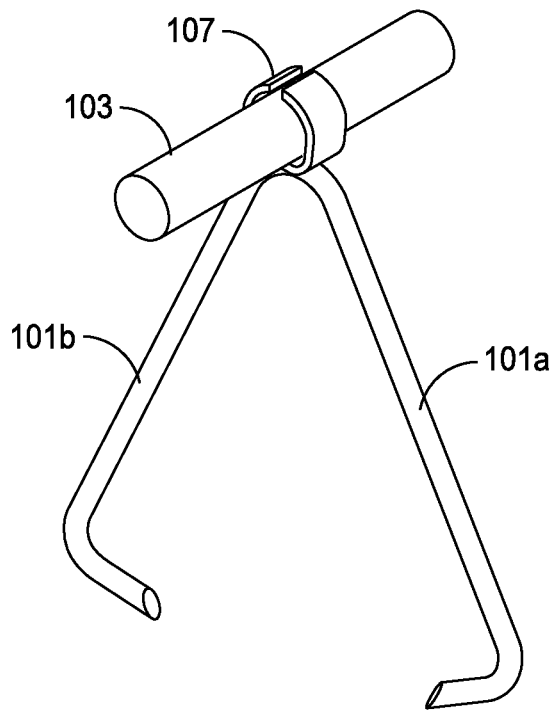
FIG. 7A is a perspective view of the device with an open carrier element that supports the brachytherapy radiation source at the joined proximal ends of the legs.
Figure 7B:
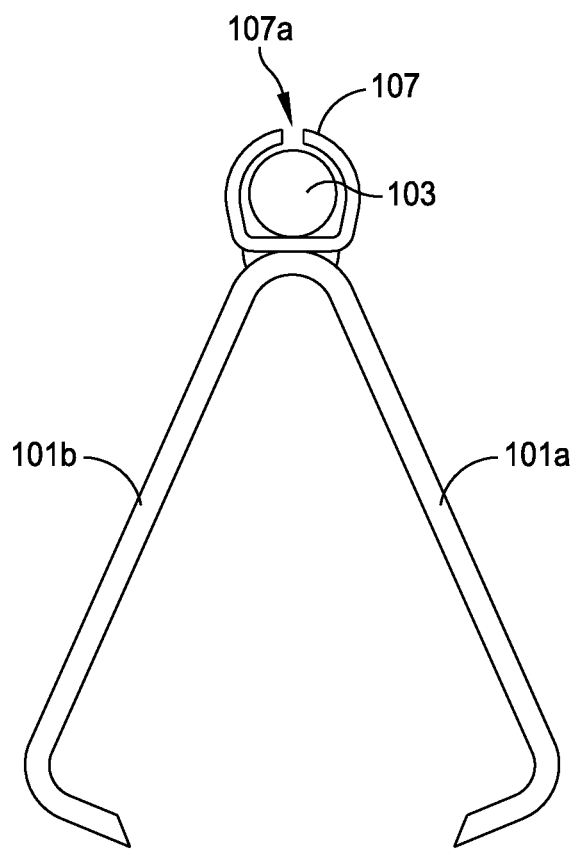
FIG. 7B is a front view of the device of FIG. 7A.
Figure 7C:
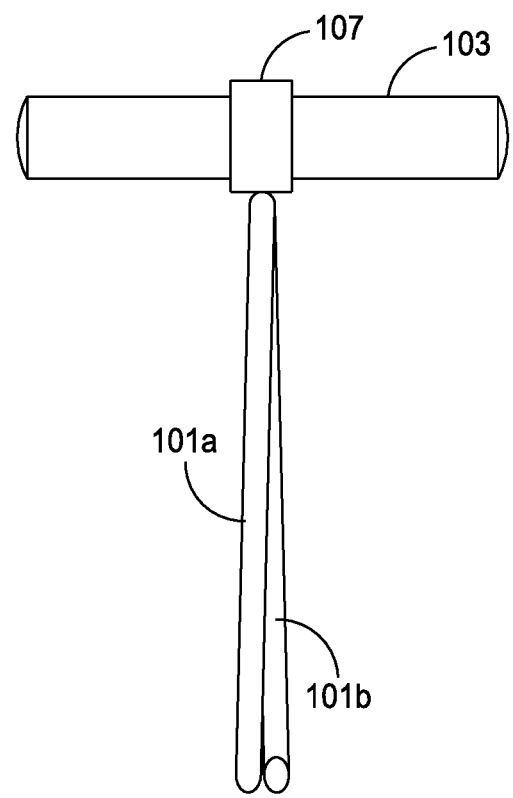
FIG. 7C is a side view of the device of FIG. 7A.

In another embodiment, the carrier element does not need to encircle the entire brachytherapy source. "Open" carrier elements that encircle at least more than 180 degrees of the circumference of the brachytherapy source can be used as shown in FIGS. 7A-7C. FIG. 7A is a perspective view of the device 100 with an open carrier element 107 that supports the brachytherapy radiation source 103 at the joined proximal ends of the legs 101a, 101b. FIG. 7B is a front view of the device 100 with the open carrier element 107 that supports the brachytherapy radiation source 103. The carrier element 107 includes an opening 107a. The opening 170a provides flexibility for the insertion of the source 103 into the carrier element 107. The carrier element 107 is tangentially attached to the span section connected at the proximal ends of the legs 101a, 101b. FIG. 7C is a side view of the carrier element 107 attached to the span section connected at the proximal ends of the legs 101a, 101b.

Figure 8A:
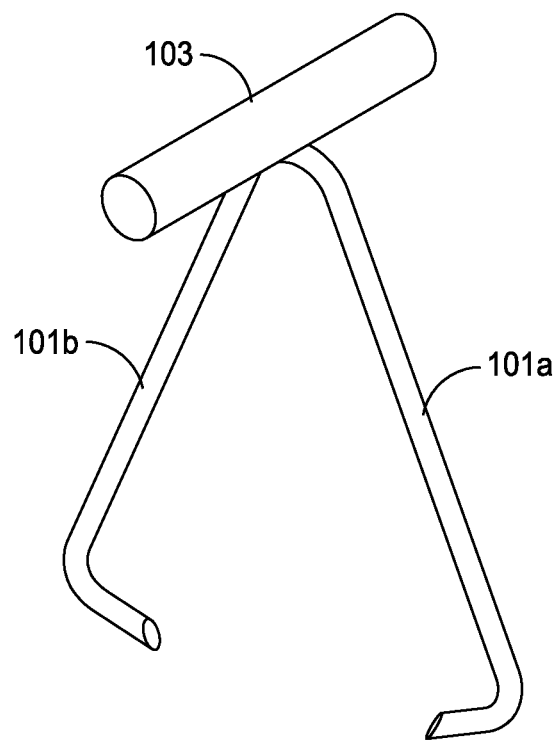
FIG. 8A is a perspective view of the device having a brachytherapy source attached directly to the span section of the legs.
Figure 8B:
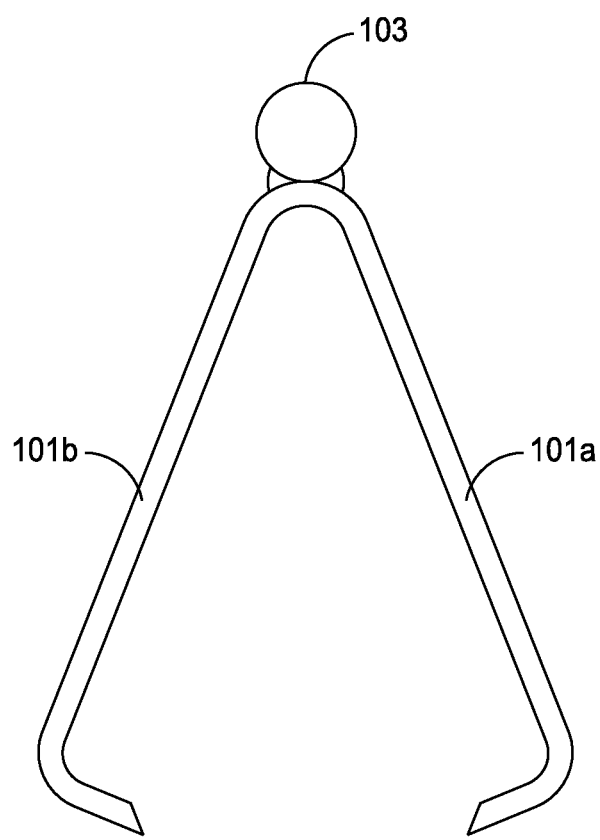
FIG. 8B is a front view of the device of FIG. 8A.
Figure 8C:
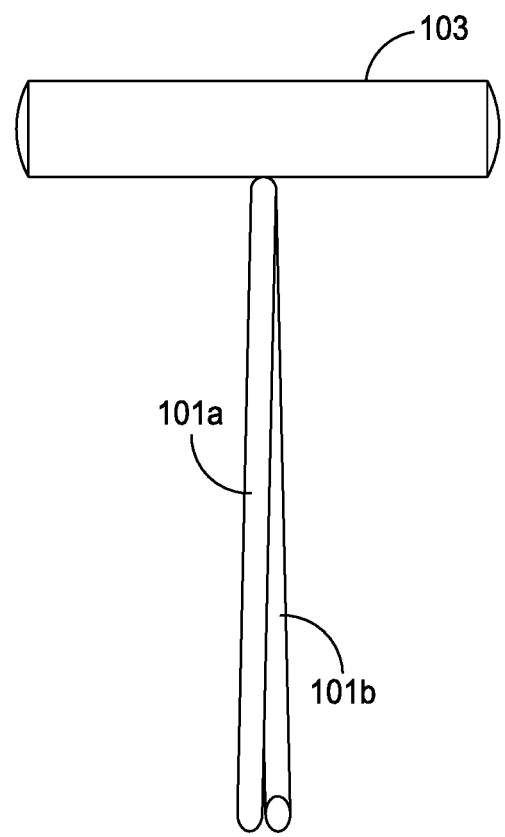
FIG. 8C illustrates a side view of the device of FIG. 8A.

In some embodiments, the carrier element may be omitted, and the source may be attached directly to the joined proximal ends of the legs. The brachytherapy source 103 can be attached directly to the wire form as shown in FIGS. 8A-8C. FIG. 8A is a perspective view of the device having a brachytherapy source 103 attached directly to the span section of the legs 101a, 101b. The source 103 can be attached tangentially to the joined proximal ends of the legs 101a, 101b as shown in FIG. 8B, illustrating a front view of the device with the source 103 directly attached to the tissue-piercing legs 101a, 101b. FIG. 8C illustrates a side view of the device with the source directly attached to the tissue-piercing legs.

The source 103 is shown attached to the wire form, however it will be appreciated that the source is separable from the attachment device (e.g., attachment member 120 shown in FIG. 1B). The source can be joined to the attachment device (or another part of the brachytherapy source delivery device such as the carrier tube) in the clinic or other medical environment performing the brachytherapy treatment at the time of the device deployment. Clinics or other facilities can maintain an inventory of attachment devices and sources, which can be used for other procedures. This provides an advantage over permanently affixed sources, which require the requisite number of devices to be specifically ordered for a procedure. After a relatively short period of time, these sources decay and cannot be used. Thus, attachment at time of treatment has significant advantages. The source can be attached via welding or other adhesive or can be formed by stamping and/or bending a strip of material, by machining or by casting and/or molding.

In the aforementioned embodiments, the axis of the brachytherapy source has been shown to be approximately perpendicular to the plane of the wire form. However, in these aforementioned or other embodiments, the brachytherapy source can be positioned parallel to the plane of the wire form, or at any angle between perpendicular and parallel, as shown on FIGS. 9A-9C. As shown in FIGS. 9A-9C, the axis of the brachytherapy source is approximately parallel to the plane of the wire form. FIG. 9A is a perspective view of the carrier element 105 and brachytherapy source 103 approximately parallel to the plane of the wire form. FIG. 9B is a front view of the carrier element 105 and brachytherapy source 103. FIG. 9C is a side view of the carrier element 105 and brachytherapy source 103 approximately parallel to the plane of the wire form.

Although shortened tube 105 is shown, any of the carrier elements disclosed herein may be implemented at the approximately parallel configuration.

In the aforementioned embodiments, the brachytherapy source has been shown to be centered on the plane of the wire form. However, in other embodiments, wire form can be positioned centered on the plane of the brachytherapy source wire form, at the extreme end of the brachytherapy source or at any position between, as shown on FIGS. 10A-10C. In this embodiment, the carrier element 105 and source 103 are shown positioned at an angle of approximately 45-degrees with respect to the plane of the wire form. Any other value for the angle can be implemented, as will be appreciated. FIG. 10A is a perspective view of an axis of the carrier element 105 and source 103 at a predetermined angle with respect to the plane of the wire form. FIG. 10B is a front view of an axis of the carrier element 105 and source 103 positioned at a predetermined angle with respect to the plane of the wire form. FIG. 10C is a side view of the axis of the carrier element 105 and source 103 positioned at a predetermined angle with respect to the plane of the wire form.

Figure 11A:
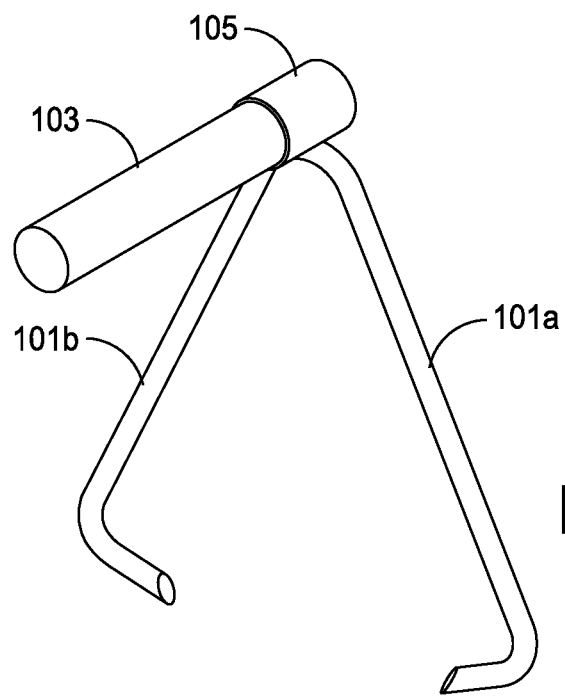
FIG. 11A is a perspective view of the device with a carrier element supporting a source tangentially with respect to the proximal ends of the legs.
Figure 11B:
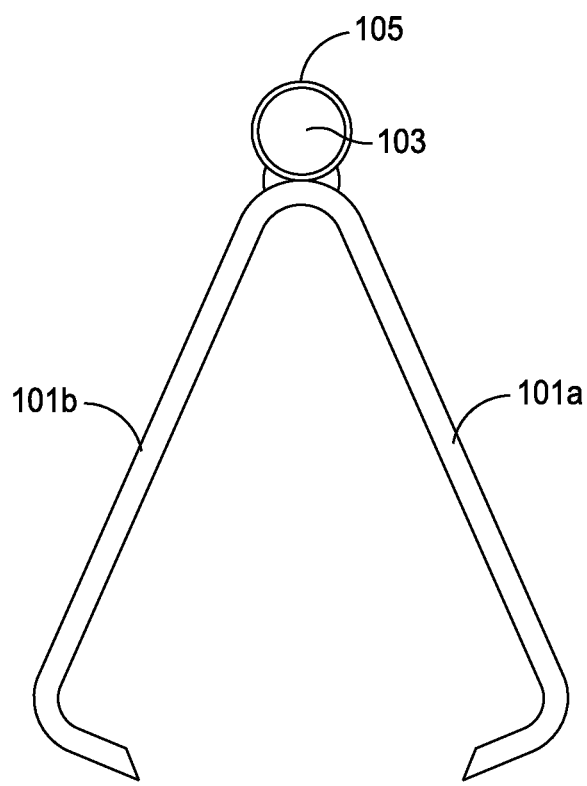
FIG. 11B is a front view of the device of FIG. 11A.
Figure 11C:
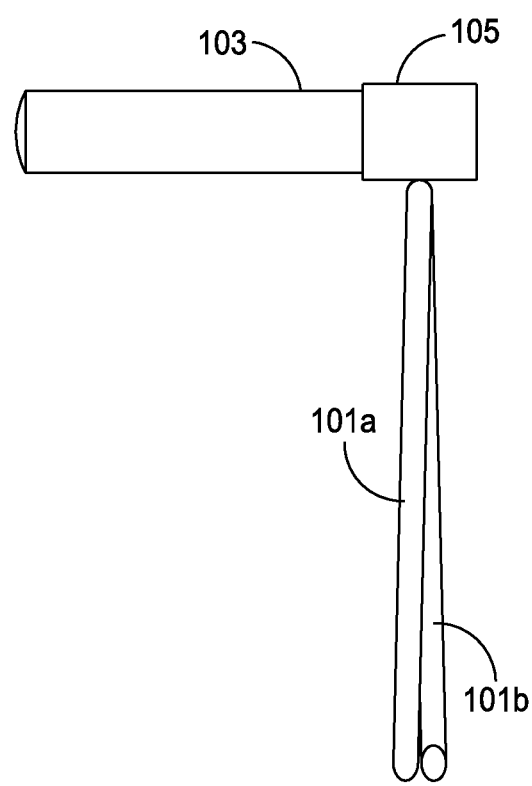
FIG. 11C is a side view of the device of FIG. 11A.

In some embodiments, it may be desirable for the source to be positioned so that it is not central within the carrier element 105, however rather extends from the carrier element 105 so that the majority of the source 103 is on one side of the element 105. FIG. 11A is a perspective view of the device 100 with a carrier element 105 supporting a source 103 tangentially with respect to the proximal ends of the legs 101a, 101b. FIG. 11B is a front view of the device with the carrier element supporting a source 103 on its end, and tangentially with respect to the proximal end of the legs 101a, 101b. FIG. 11C is a side view of the device with the carrier element 105 supporting a source 103 on its end, and tangentially with respect to the proximal end of the legs 101a, 101b.

Figure 12A:
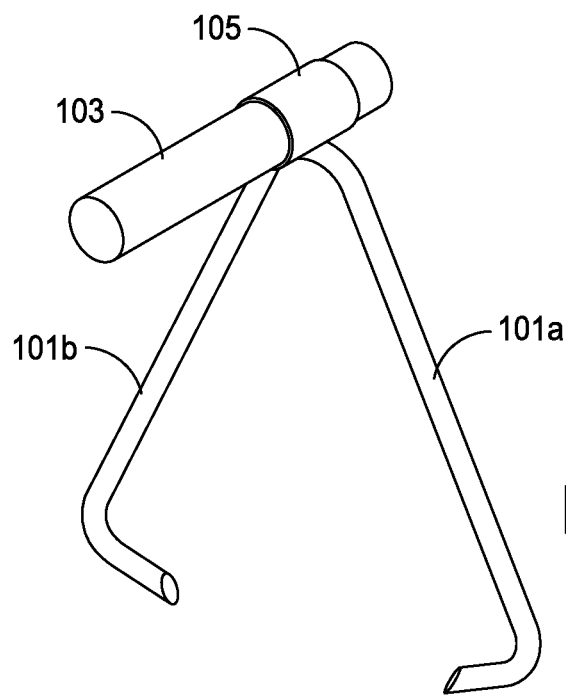
FIG. 12A shows a perspective view of the carrier element supporting the source at a point proximate the end of the source.
Figure 12B:
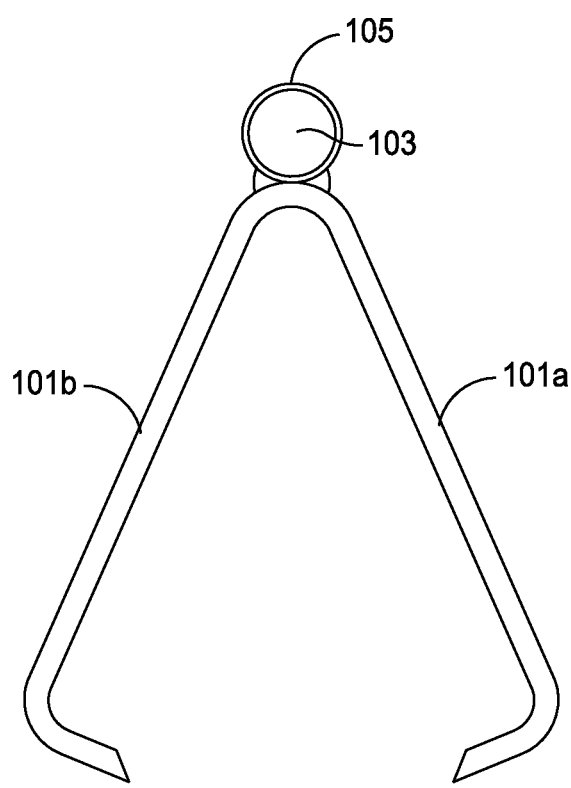
FIG. 12B shows a front view of the device of FIG. 12A.
Figure 12C:
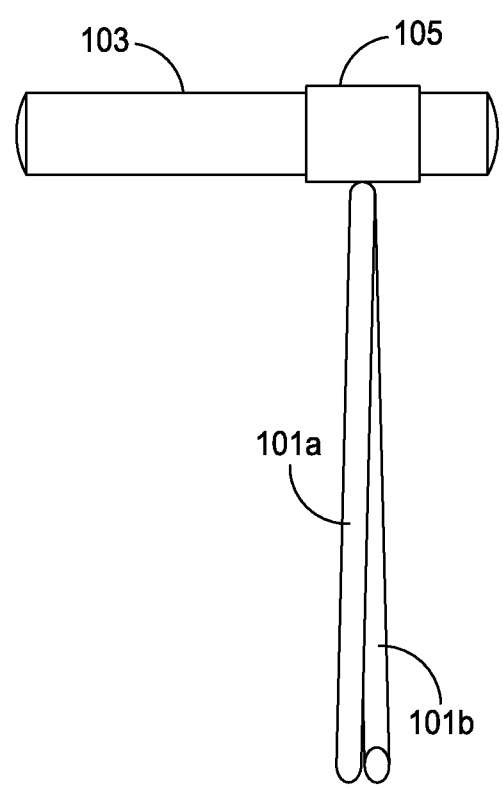
FIG. 12C shows a side view of the device of FIG. 12A.

In some embodiments, it may be desirable for the source to be positioned so that a certain predetermined amount of the source is extending from one side of the carrier element 105, and another amount of the source is extending out from the other side of the carrier element 105, as shown in FIGS. 12A-12C. FIG. 12A shows a perspective view of the carrier element 105 supporting the source 103 at a point proximate the end of the source, however not at the extreme end of the source, so as to allow for an amount of the source to extend from each side of the carrier element, whilst not being in the direct center of the carrier element. FIG. 12B shows a front view of the carrier element 105 supporting the source 103 at the end of the source. FIG. 12C shows a side view of the carrier element 105 supporting the source 103 at the end of the source.

Figure 13D:
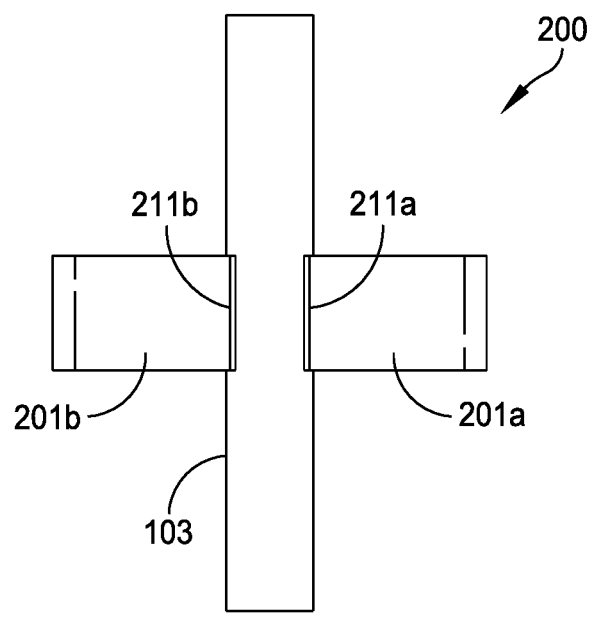
FIG. 13D shows a top view of the device of FIG. 13A.
Figure 13E:
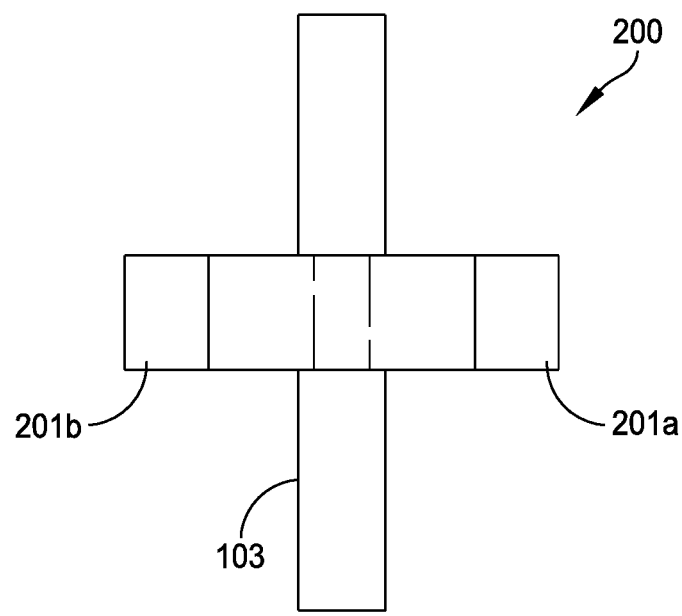
FIG. 13E shows a bottom view of the device of FIG. 13A.

In the aforementioned embodiments, the wire form has been shown to have a generally round cross-sectional shape. However, in other embodiments, the wire form can have rectangular, or other shape, cross sections. Also, the legs of the wire form do not necessarily need to be positioned straight from the point of connection with the carrier. Other shapes can be used, as shown in FIGS. 13A-13C. FIG. 13A shows a perspective view of a device 200 having a generally rectangular cross-sectional shape. The device 200 includes first and second tissue-piercing legs 201a. 201b which are joined together at a proximal end, and have barbs formed at a distal end of each tissue-piercing leg. The proximal ends of the legs 201a, 201b are joined together at a span section 215. The span section 215 has a first ear 211a and a second ear 211b extending therefrom, which together support the brachytherapy radioactive source 103. FIG. 13B is a front view of the device showing the first and second tissue-piercing legs 201a, 201b, having ears 211a, 211b extending from the proximal ends of the legs 201a, 20b where they are joined together. FIG. 13C is a side view of the device showing the first tissue-piercing leg 201a with ear 211a extending from the distal end of the leg 201a, which supports the source 103.

Figure 14:
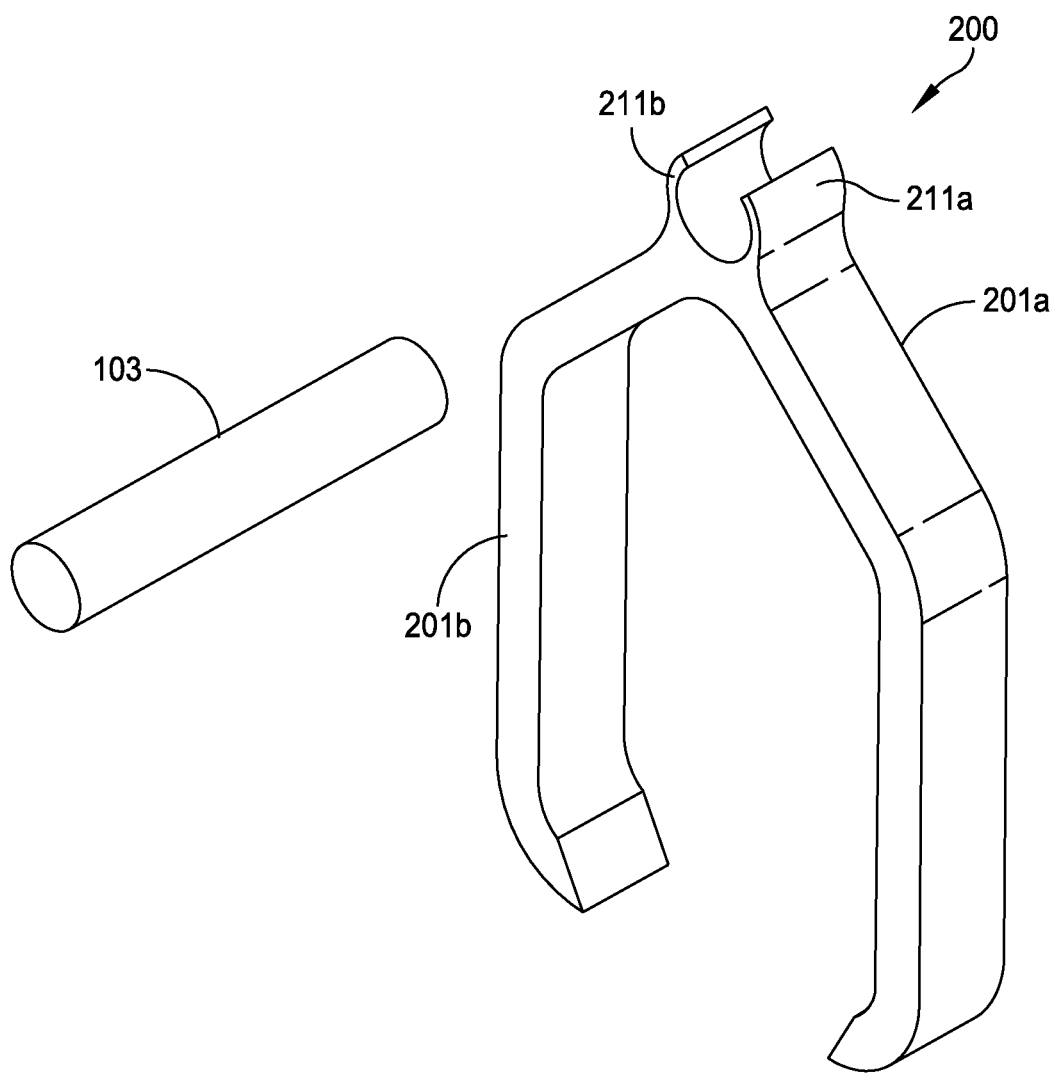
FIG. 14 illustrates a perspective view of the rectangular cross-sectional device with the source prior to being supported by the ears of the device.

In the aforementioned embodiments, the carrier has been attached to the wire form. However, in other embodiments, it is possible to have the carrier be part of the wire form, either by machining or bending, as shown on FIGS. 13A-14. FIG. 14 illustrates a perspective view of the rectangular cross-sectional device 200 with the source 103 prior to being supported by the ears 211a, 211b of the device 200. The ears 211a, 211b may be considered the "carrier element" according to the present disclosure and are formed as an integral piece with the tissue-piercing legs 210a, 201b to provide a unitary structure (without the source, or with the source when attached).

Figure 15A:
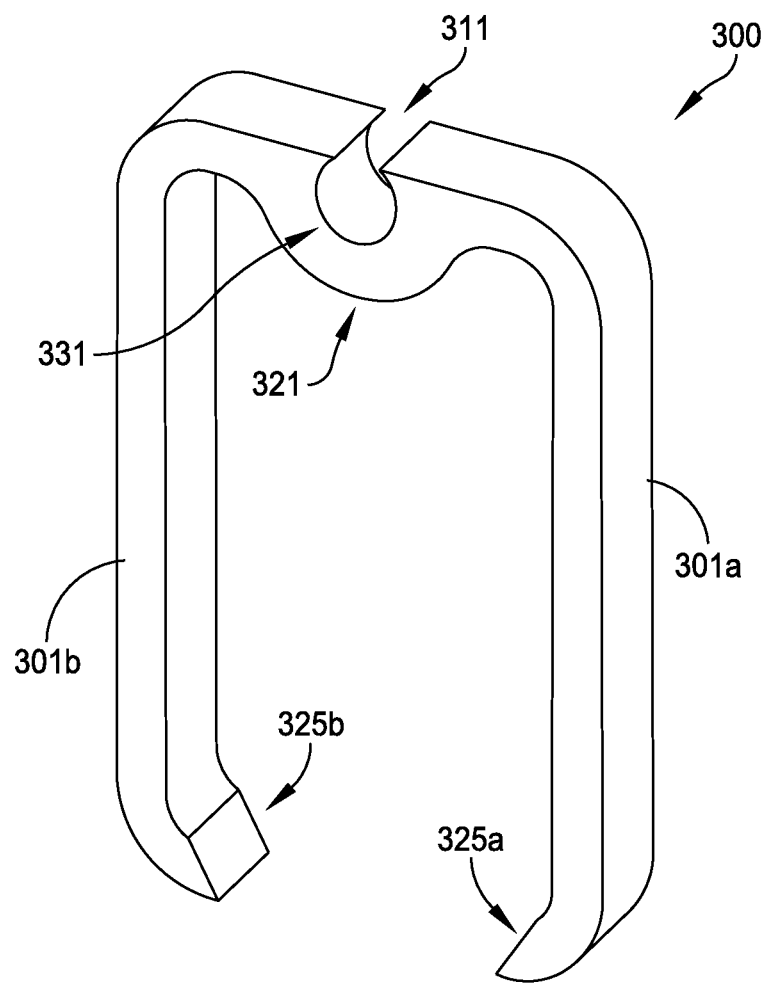
FIG. 15A illustrates a perspective view of another embodiment where the carrier element is formed integral as part of the wire form, either by machining or bending, according to a rectangular cross-sectional shape of the wire form.
Figure 15B:
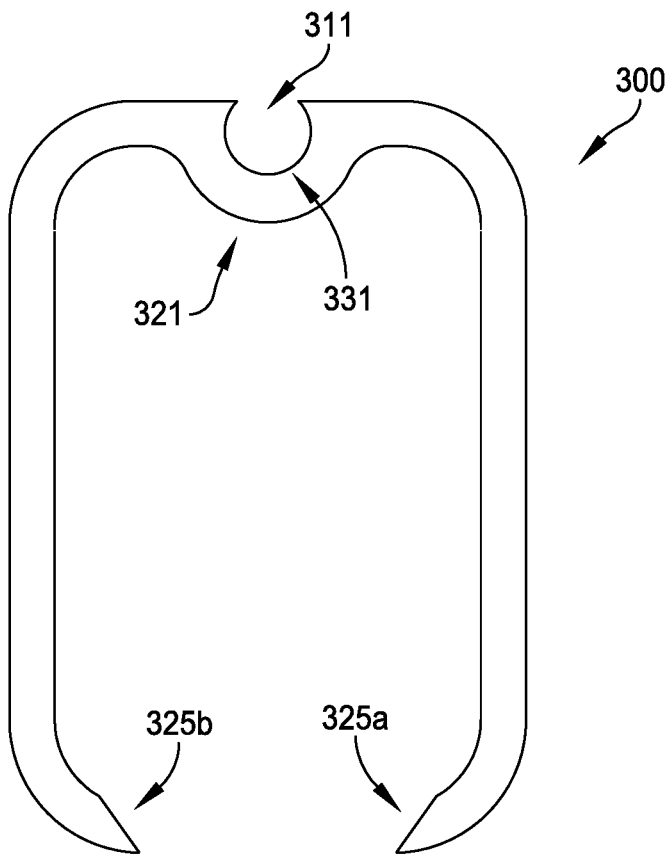
FIG. 15B illustrates a front view of the device 300.
Figure 15C:
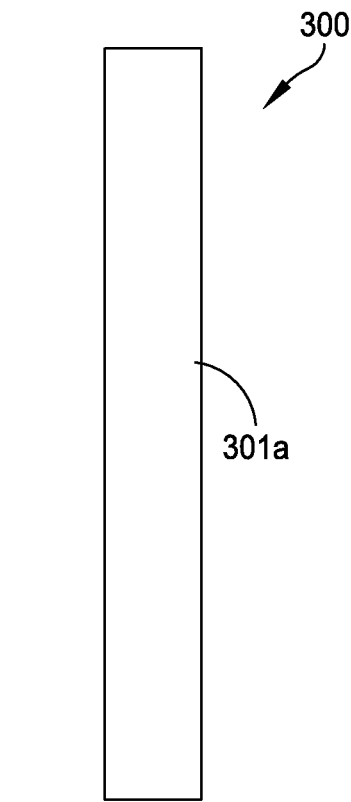
FIG. 15C illustrates a side view of the device 300.
Figure 15D:
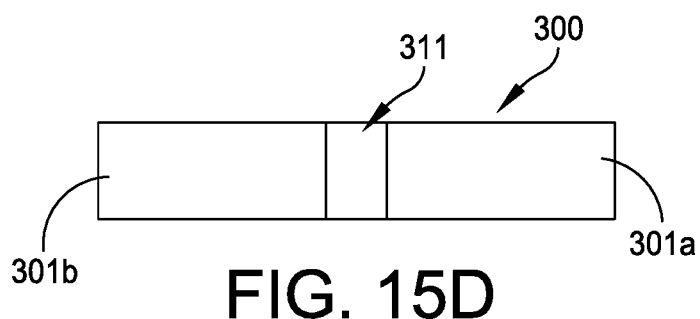
FIG. 15D illustrates a top view of the device 300.
Figure 15E:
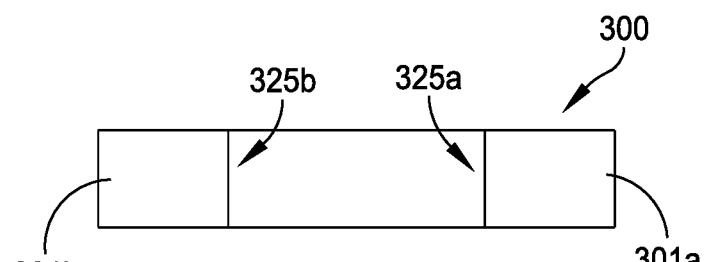
FIG. 15E illustrates a bottom view of the device 300.

FIG. 15A illustrates a perspective view of another embodiment where the carrier element is formed integral as part of the wire form, either by machining or bending, according to a rectangular cross-sectional shape of the wire form. The brachytherapy source delivery device 300 includes a first tissue-piercing leg 301a and a second tissue piercing leg 301b joined together at a span section 321. A carrier element 331 is formed in the span section 321 and has an opening 311. The source (e.g., source 103 shown herein) can be supported by the carrier element 331. In this embodiment, the legs 301a, 301b extend in an approximately straight orientation from the span section 321, and the legs 301a, 301b have barbs 325a, 325b, respectively extending therefrom. FIG. 15B illustrates a front view of the device 300. FIG. 15C illustrates a side view of the device 300. FIG. 15D illustrates a top view of the device 300. FIG. 15E illustrates a bottom view of the device 300.

Although a rectangular cross-sectional shape for the wire form is shown in FIG. 15 it will be appreciated that a likewise structure can be implemented having another cross-sectional shape, such as circular or square, or other non-circular shape.

In the aforementioned embodiments, the carrier has been positioned on the "outside" of the wire form. Meaning, the wire form has an exterior surface that has supported the source and an interior surface toward which the barbs are oriented. However, in other embodiments, it is possible to have the carrier be positioned "inside" the wire form and in same general orientation inward toward the barbs, as shown in FIGS. 16A-16B.

Figure 16A:
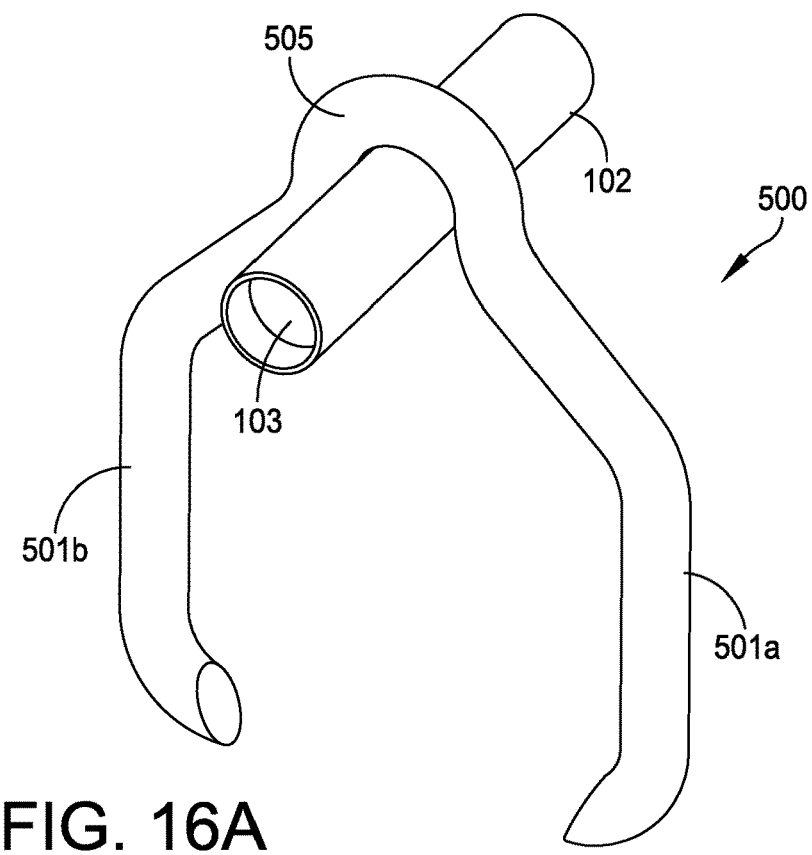
FIG. 16A is a perspective view of a device having first and second tissue-piercing legs in a generally circular cross-sectional wire form shape, with the proximal ends of the legs joined together at a span section.

FIG. 16A is a perspective view of a device 500 having first and second tissue-piercing legs 501a, 501b in a generally circular cross-sectional wire form shape, with the proximal ends of the legs joined together at a span section 505. The span section supports the carrier element 102 on an interior surface thereof as shown. The source 103 is supported by the carrier element 102.

Figure 16B:
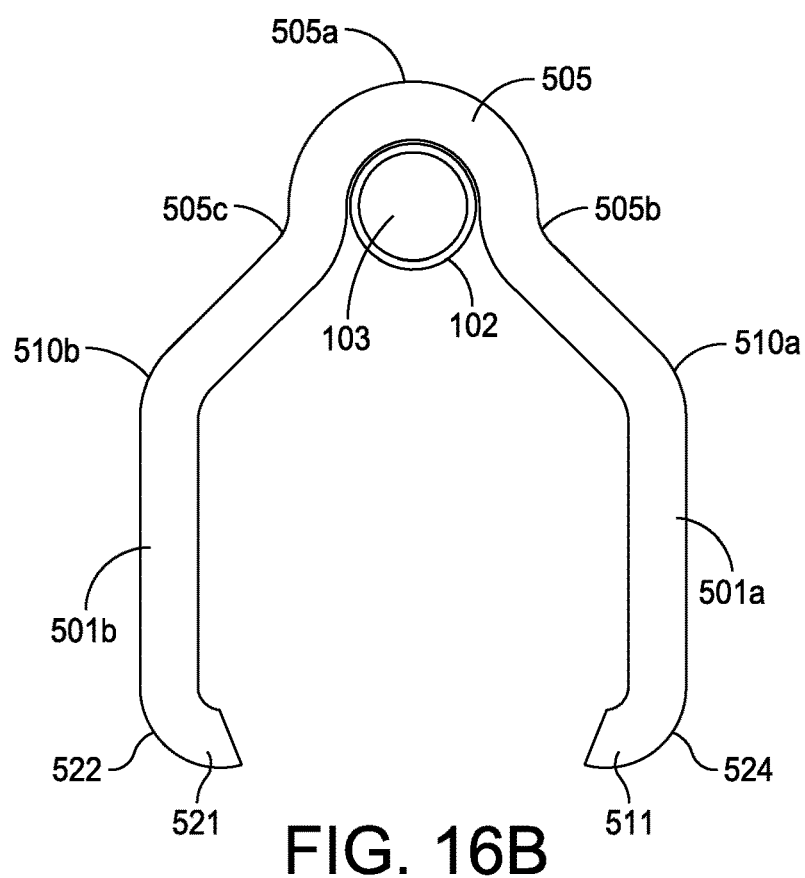
FIG. 16B is a side view of the device of FIG. 16A.

FIG. 16B is a side view of the device 500 having first and second tissue-piercing legs 501a, 501b joined together at a span section 505 at proximal ends of the legs 501a, 501b. The device 500 includes the upper span section 505 having a first convex curved surface 505a, which is joined to two concave curved surfaces 505b, 505c. The concave curved surface 505c is joined to another convex curved surface 510b, which is connected to the leg portion 501b, secured to another concave curved surface 522, and to a barb 521. The concave curved surface 505b is joined to another convex curved surface 510a, which is connected to the leg portion 510a, secured to another concave curved surface 524, and to a barb 511.

FIG. 16C is a front view of the device 500 without the course attached. FIG. 16D is a top view of the device 500. FIG. 16E is a bottom view of the device 500. FIG. 16F is a side view of the device 500.

In the aforementioned embodiments, the ends of the wire form that pierce the tissue have been shown to have a wedge-shaped end for the distal end of the legs where the barbs are formed. However, it is possible for the tissue-piercing end to be conical, barbed, or, because of the small size of the wire, even flat, as shown in FIGS. 17A-17D.

Figure 17A:
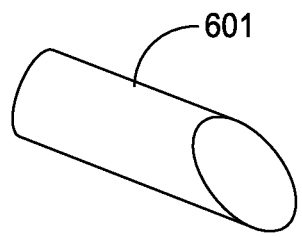
FIGS. 17A-17D illustrate various shapes for the tissue-piercing end of the legs.
Figure 17B:
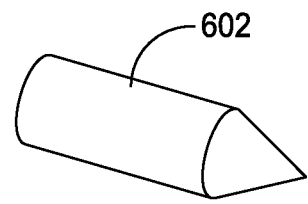
Figure 17C:
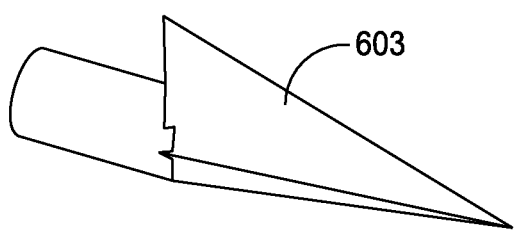
Figure 17D:
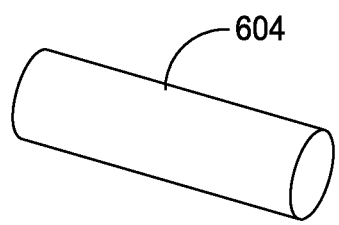

FIG. 17A illustrates a tissue-piercing end 601 that has a wedged surface as a shape. FIG. 17B illustrates a tissue-piercing end 602 that is conical in shape. FIG. 17C illustrates a tissue-piercing end 603 that is barbed in shape at the distal end. FIG. 17D illustrates a tissue-piercing end 604 that is flat at the distal end.

Figure 18:
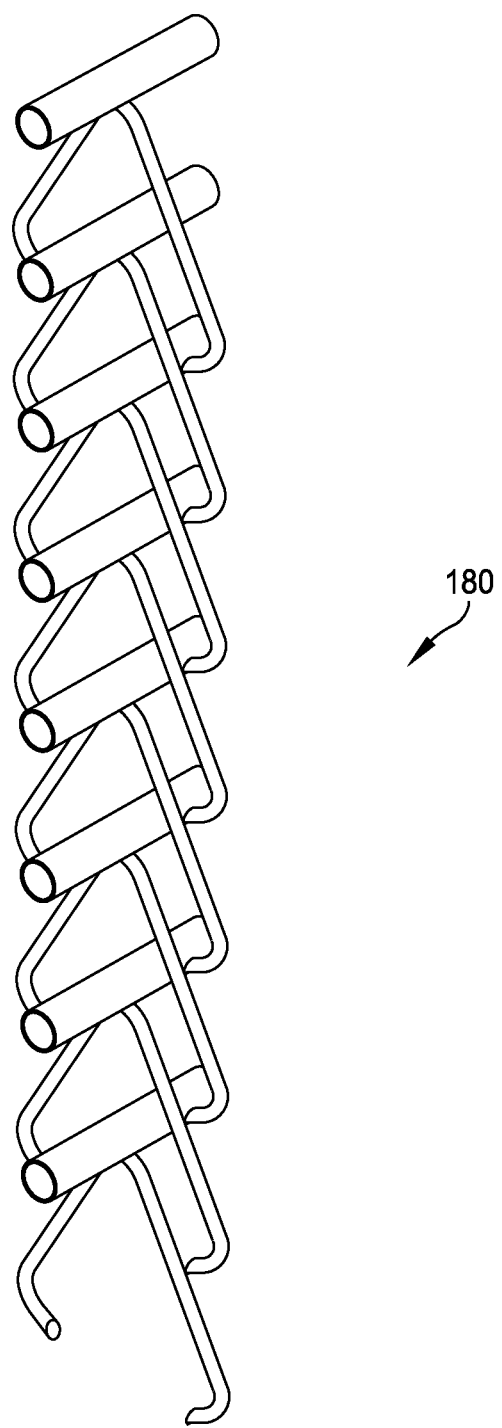
FIG. 18 illustrates a stack of the devices according to an embodiment.

FIG. 18 illustrates a stack 180 of the devices according to an embodiment, with the source perpendicular to the plane of the wire, for example as shown in FIG. 1A. The stack 180 comprises a plurality of devices that are arranged together as they would appear in a delivery applicator.

Figure 19:
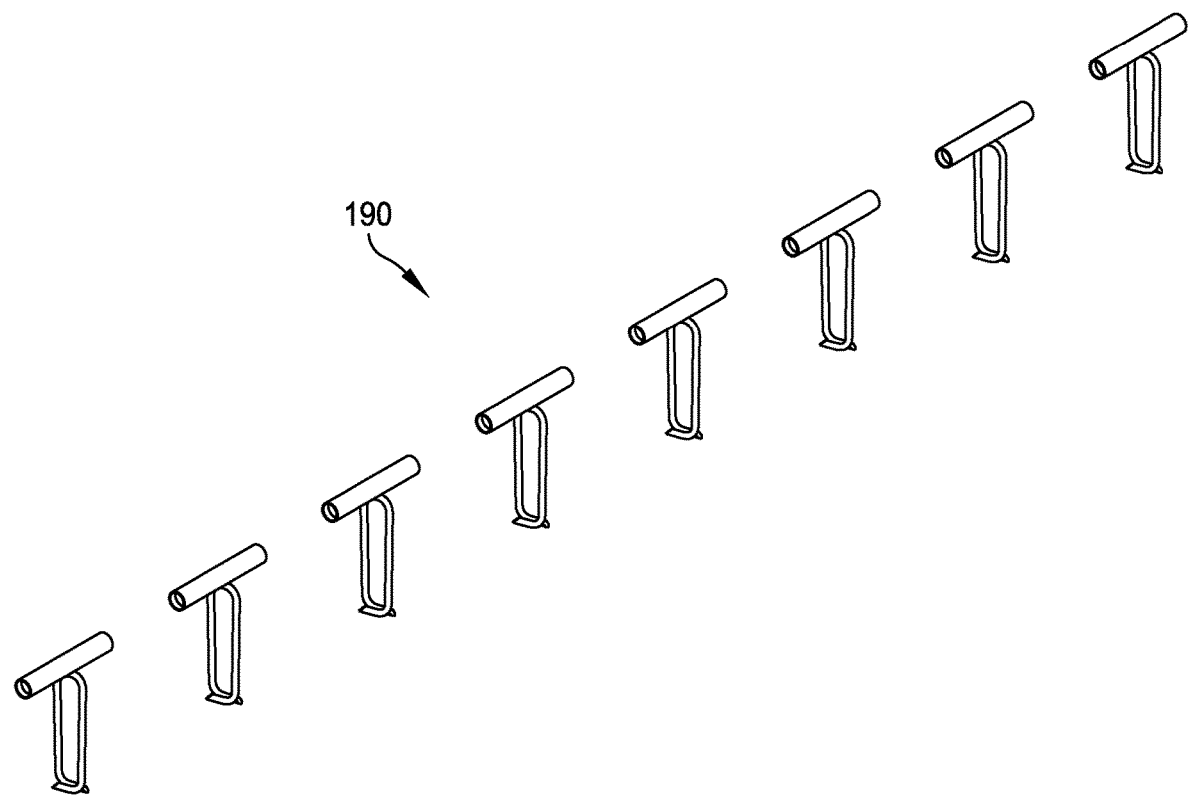
FIG. 19 illustrates a stack of the devices according to an embodiment.

FIG. 19 illustrates a stack 190 of the devices according to an embodiment, with the source perpendicular to the plane of the wire, for example as shown in FIG. 3A in the closed position. The stack 190 illustrates how the devices would appear when positioned within a patient.

Figure 20:
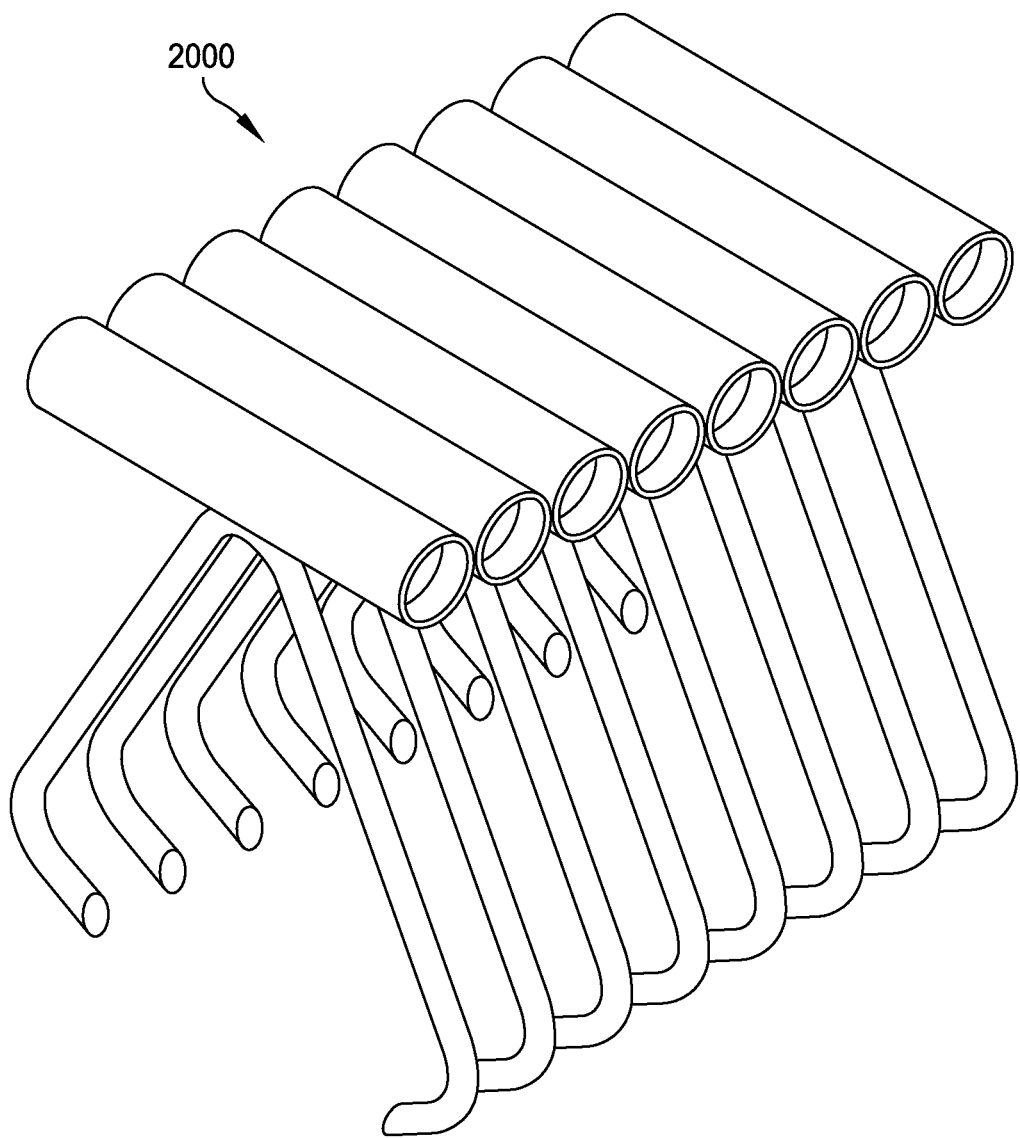
FIG. 20 illustrates a stack of the devices according to an embodiment.

FIG. 20 illustrates a stack of the devices according to an embodiment, with the source parallel to the plane of the wire, for example as shown in FIG. 9A. FIG. 20 illustrates the stack 2000 as it would appear in a delivery applicator.

Figure 21:
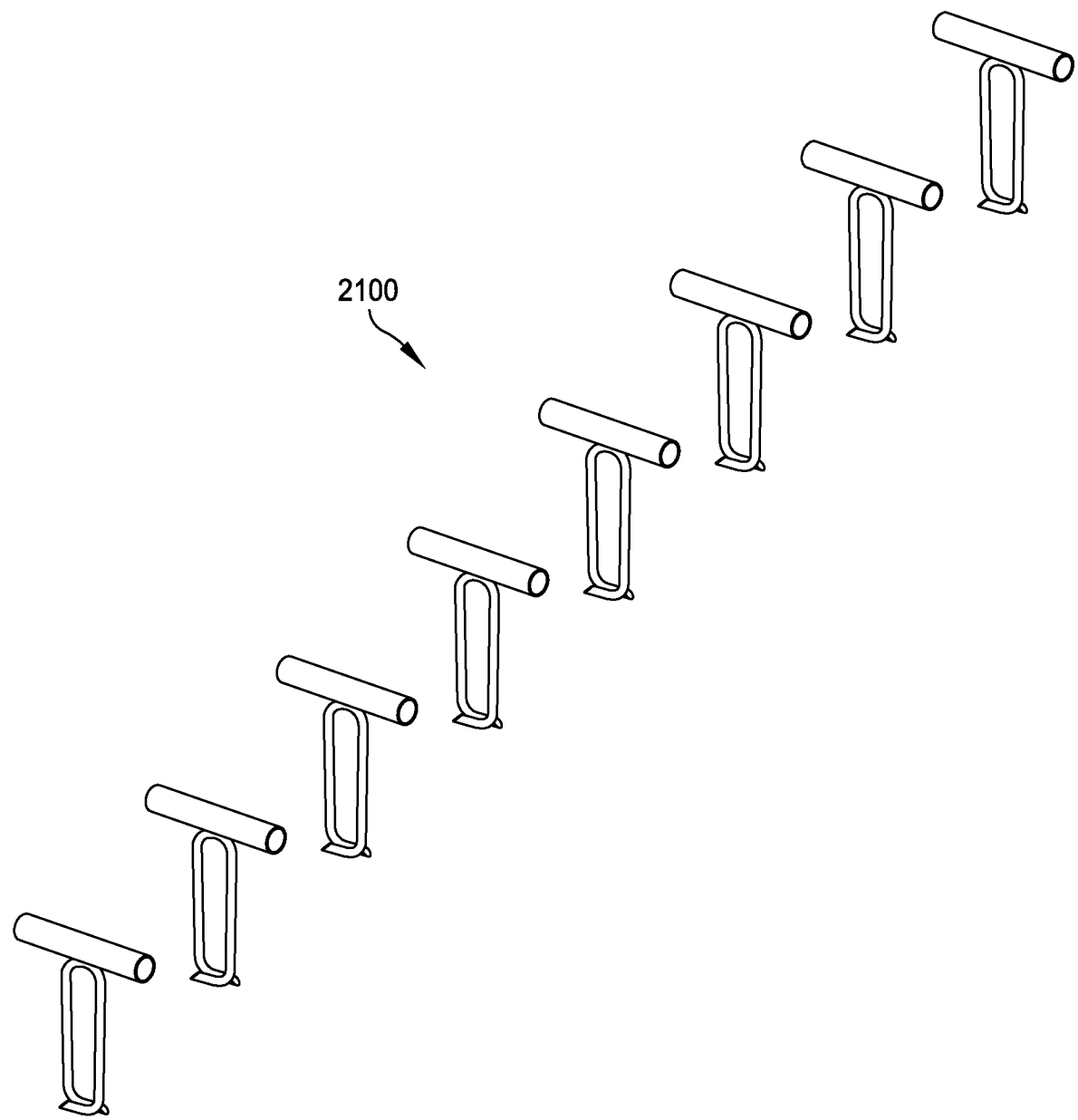
FIG. 21 illustrates a stack of the devices according to an embodiment.

FIG. 21 illustrates a stack of the devices according to an embodiment with the source parallel to the plane of the wire, for example as shown in FIG. 9A. FIG. 21 illustrates the stack 2100 as it would appear when positioned in the patient.

Figure 22A:
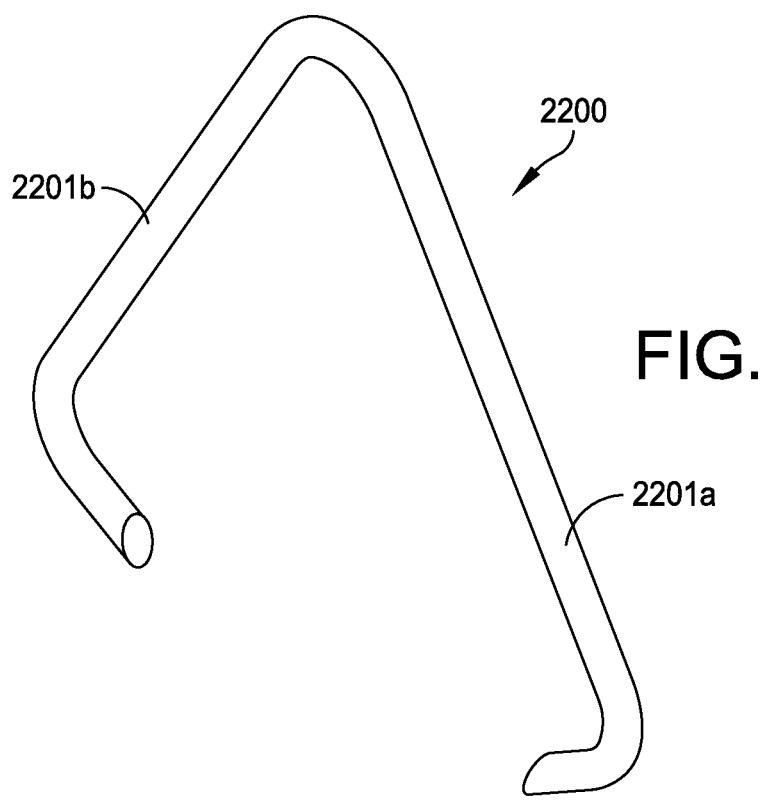
FIG. 22A illustrates a perspective view of a brachytherapy source delivery device having tissue-piercing legs with a brachytherapy source incorporated into the legs.

FIG. 22A illustrates a perspective view of a brachytherapy source delivery device 2200 having tissue-piercing legs 2201a, 2201b with a brachytherapy source incorporated into the legs. Refer to FIG. 22F showing the sources incorporated into the legs. In this embodiment, there are six individual sources incorporated into the legs, with three sources in each leg, however any number of sources may be implemented.

Figure 22B:
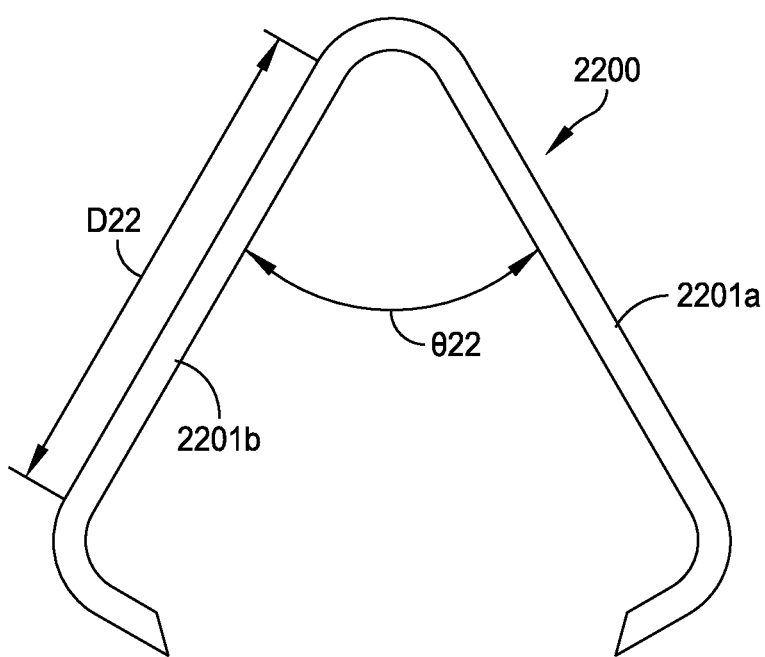
FIG. 22B illustrates a front view of the device of FIG. 22A.

FIG. 22B illustrates a front view of the device 2200 of FIG. 22A. The device 2200 includes first and second tissue-piercing legs 2201a, 2201b. The length of the leg 2201b can be a distance D22 of approximately 4.8 centimeters (cm), and generally has the length of 2.4-4.8 cm; however any length can be implemented depending upon the particular application and/or patient involved. The angle θ22 is approximately 60-degrees, and can be in the range of 60-120 degrees.

Figure 22C:
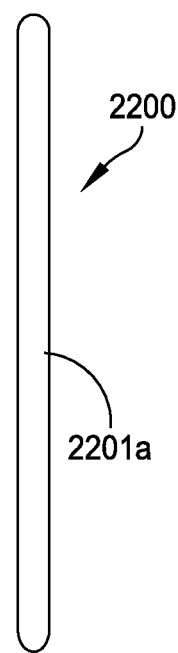
FIG. 22C illustrates a side view of the device of FIG. 22A.
Figure 22D:
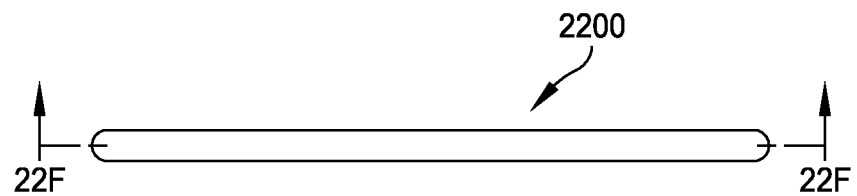
FIG. 22D illustrates a side view of the device of FIG. 22A.
Figure 22E:
FIG. 22E illustrates a bottom view of the device of FIG. 22A.
Figure 22F:
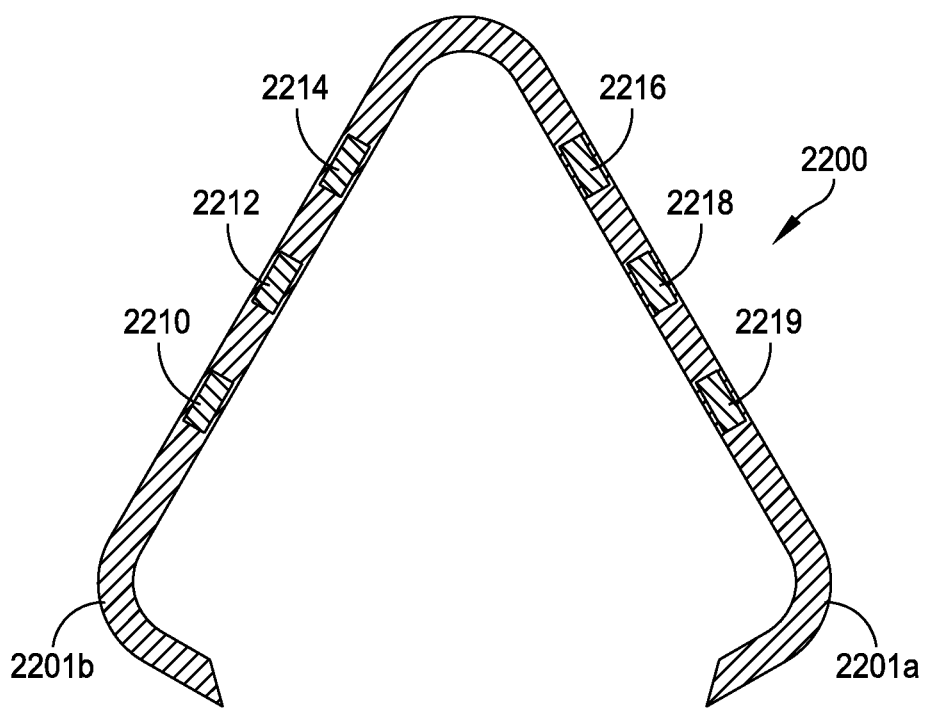
FIG. 22F illustrates a cross-sectional view as taken along line 22F-22F of FIG. 22D.

FIG. 22C illustrates a side view of the device 2200 of FIG. 22A. FIG. 22D illustrates a side view of the device 2200 of FIG. 22A. FIG. 22E illustrates a bottom view of the device 2200 of FIG. 22A.

Figure 23A:
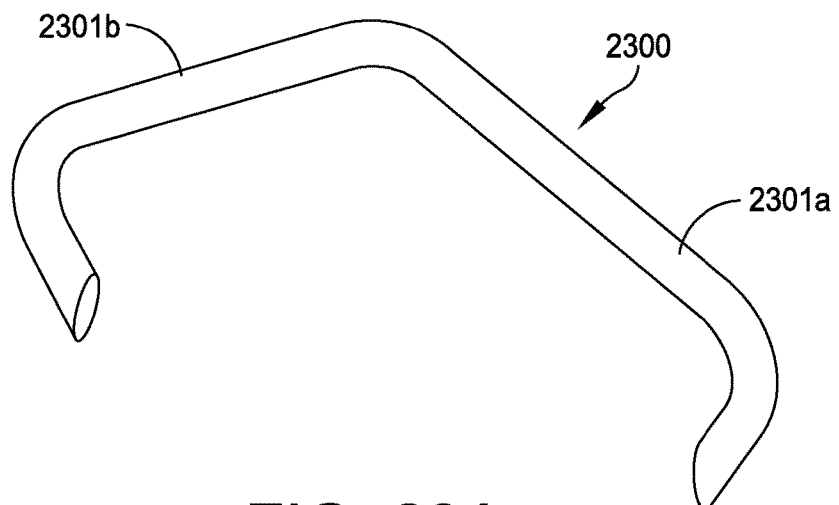
FIG. 23A illustrates a perspective view of a brachytherapy source delivery device having tissue-piercing legs with a brachytherapy source incorporated into the legs.

FIG. 22F illustrates a cross-sectional view as taken along line 22F-22F of FIG. 22D. As shown, there are six radioactive sources 2210, 2212, 2214, 2216, 2218, and 2219, with three radioactive sources 2210, 2212 and 2214 in the tissue-piercing leg 2210b, and sources 2216, 2218, and 2219 in the tissue-piercing leg 2210a. It will be appreciated that the position and placement of the sources within the legs can be variable depending upon the particular application and/or patient and/or tissue site FIG. 23A illustrates a perspective view of a brachytherapy source delivery device 2300 having tissue-piercing legs 2301a, 2301b with a brachytherapy source (not shown in FIG. 23A) incorporated into the legs. The legs can have a length D23 that is approximately 2.4 cm, however this can be approximately 2.4-4.8 cm. The angle θ23 can be approximately 120-degrees, or can be in the range of 60-120 degrees.

Figure 23B:
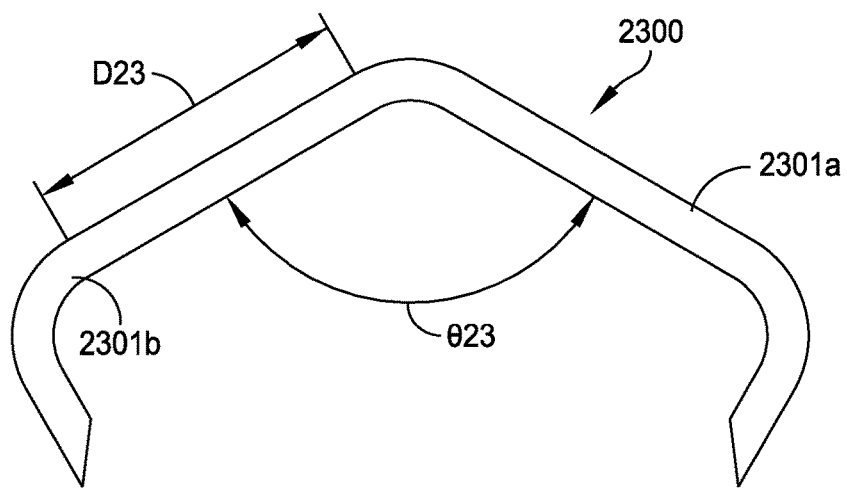
FIG. 23B illustrates a front view of the device of FIG. 23A.
Figure 23C:
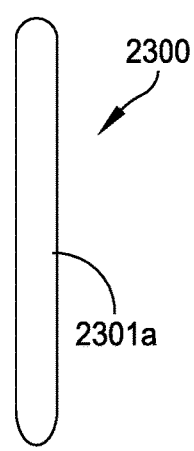
FIG. 23C illustrates a side view of the device of FIG. 23A.
Figure 23D:
FIG. 23D illustrates a top view of the device of FIG. 23A.
Figure 23E:
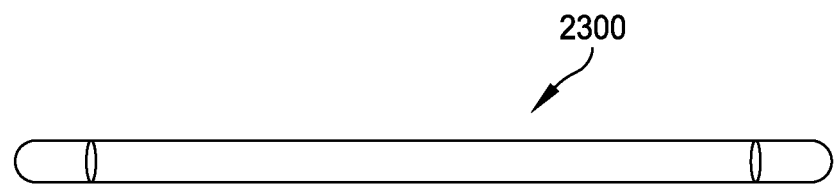
FIG. 23E illustrates a bottom view of the device of FIG. 23A.

FIG. 23B illustrates a front view of the device 2300 of FIG. 23A. FIG. 23C illustrates a side view of the device 2300 of FIG. 23A. FIG. 23D illustrates a top view of the device 2300 of FIG. 23A. FIG. 23E illustrates a bottom view of the device 2300 of FIG. 23A.

Various embodiments discussed herein may be combined with each other in appropriate combinations in connection with the system described herein.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A brachytherapy source delivery device comprising:
a first tissue-piercing leg having proximal and distal ends;
a second tissue-piercing leg having proximal and distal ends, wherein the proximal ends of the first and second tissue-piercing legs are joined at a span section in a first angular orientation with respect to each other; and a carrier element formed at, or attached to, the span section, the carrier element configured to support a radioactive brachytherapy source;

each of said first and second tissue-piercing legs comprising a straight and longitudinally extending leg each having at the distal end thereof a barb, and wherein the respective barbs extend in a direction toward each other;

said span section comprising only an arcuate span section having respective ends that are contiguous with the respective proximal ends of the first and second tissue-piercing legs;

wherein each of the first and second tissue-piercing legs have a like straight length that is greater than an arcuate length of the arcuate span section.

2. The brachytherapy source delivery device of claim 1, wherein the distal ends of the first and second legs are curved inward toward each other and configured to pierce a tissue when engaged toward each other into a closed position.

3. The brachytherapy source delivery device of claim 1, wherein the first and second tissue-piercing legs are formed of a wire having a circular cross-sectional shape.

4. The brachytherapy source delivery device of claim 1, wherein the first and second tissue-piercing legs are formed of a wire having a non-circular cross-sectional shape.

5. The brachytherapy source delivery device of claim 1, wherein the carrier element is formed as part of a unitary structure with the first and second tissue-piercing legs.

6. The brachytherapy source delivery device of claim 1, wherein the carrier element comprises a tube having a circular or non-circular cross-sectional shape.

7. The brachytherapy source delivery device of claim 1, wherein the carrier element extends along a full length of the radioactive brachytherapy source.

8. The brachytherapy source delivery device of claim 1, wherein the carrier element has an opening at a top portion of the carrier element.

9. The brachytherapy source delivery device of claim 1, further comprising a radiation shield disposed on the carrier element.

10. The brachytherapy source delivery device of claim 1, wherein the carrier element is tangentially attached to the span section.

11. The brachytherapy source delivery device of claim 1, wherein the length of each of the first and second tissue-piercing legs is at least two times the arcuate length of the arcuate span section.

12. The brachytherapy source delivery device of claim 1, wherein the span section defines a first curved exterior surface having an angle of approximately 90 degrees, wherein the distal end of the first leg forms a second curved exterior surface having a second angle of approximately 90 degrees, and wherein the distal end of the second leg forms a third curved exterior surface having a third angle of approximately 90 degrees.

13. The brachytherapy source delivery device of claim 1, wherein the legs are configured to be brought into a closed position from an open position in a single step.

14. A brachytherapy source delivery device that is comprised of a one piece wire member that extends in a substantial single plane, said wire member including a pair of longitudinally extending legs that each have a tissue piercing distal end, and an interconnecting span section that connects proximal ends of the respective pair of longitudinally extending legs, and a carrier element that is attached to the span section and that is configured to receive a radioactive brachytherapy source, each of said pair of longitudinally extending legs comprising a straight leg each having at the distal end thereof a barb, said span section having a semi-circular arc having respective ends that are contiguous with respective proximal ends of the pair of longitudinally extending legs; said wire member constructed and arranged having an open position in which the barbs are separated so that the barbs can circumvent a tissue site and a closed position in which the barbs engage the tissue site.

15. The brachytherapy source delivery device of claim 14 wherein, in the open position, the pair of longitudinally extending legs are disposed at an acute angle to each other, and, in the closed position, the pair of longitudinally extending legs are disposed substantially in parallel to each other.

16. The brachytherapy source delivery device of claim 15 wherein, in the closed position, the pair of longitudinally extending legs are disposed so that the respective barbs overlap each other.

17. The brachytherapy source delivery device of claim 16 wherein the carrier is a tubular member, and the tubular member extends longitudinally along a longitudinal axis that is disposed at an angle to the single plane of the wire member.

18. The brachytherapy source delivery device of claim 17 wherein the span section is arcuate and configured to continuously connect with the respective longitudinally extending legs that are of equal length so as to form a symmetric wire member.

19. The brachytherapy source delivery device of claim 18 wherein the longitudinal axis of the tubular member is disposed at substantially at a right angle to the single plane of the wire member.

20. The brachytherapy source delivery device of claim 18 wherein the longitudinal axis of the tubular member is disposed within the single plane of the wire member.

21. The brachytherapy source delivery device of claim 17 wherein, in the open position the barbs are configured to be separated so that the barbs can circumvent a tissue site and in a closed position the barbs are configured to engage and overlap at the tissue site.

* * * * *